United States Patent
Kadayam Viswanathan et al.

(10) Patent No.: US 10,466,186 B2
(45) Date of Patent: Nov. 5, 2019

(54) WORKFLOW FOR RESATURATION AND ANALYSIS OF UNCONVENTIONAL CORE SAMPLES

(71) Applicant: Schlumberger Technology Corporation, Sugar Land, TX (US)

(72) Inventors: Ravinath Kausik Kadayam Viswanathan, Sharon, MA (US); Kamilla Fellah, Brookline, MA (US); Erik Rylander, Frisco, TX (US); Philip M. Singer, Richmond, TX (US); Richard E. Lewis, Frisco, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 477 days.

(21) Appl. No.: 15/113,950

(22) PCT Filed: Jan. 21, 2015

(86) PCT No.: PCT/US2015/012136
§ 371 (c)(1),
(2) Date: Jul. 25, 2016

(87) PCT Pub. No.: WO2015/112529
PCT Pub. Date: Jul. 30, 2015

(65) Prior Publication Data
US 2016/0341680 A1    Nov. 24, 2016

Related U.S. Application Data

(60) Provisional application No. 62/005,075, filed on May 30, 2014, provisional application No. 61/931,378, filed on Jan. 24, 2014.

(51) Int. Cl.
*G01N 24/08* (2006.01)
*G01N 33/24* (2006.01)
*G01R 33/44* (2006.01)

(52) U.S. Cl.
CPC .......... *G01N 24/081* (2013.01); *G01N 33/24* (2013.01); *G01R 33/448* (2013.01)

(58) Field of Classification Search
CPC ..... G01N 24/081; G01N 33/24; G01R 33/448
(Continued)

(56) References Cited

U.S. PATENT DOCUMENTS 4,699,002 A * 10/1987 Rockley ............... E21B 49/005
73/152.07
5,200,699 A    4/1993 Baldwin et al.
(Continued)

FOREIGN PATENT DOCUMENTS

CN        101458218 A    6/2009
WO    WO2011133859 A1    10/2011
(Continued)

OTHER PUBLICATIONS

Singer et al., "1D and 2D NMR Core-Log Integration in Organic Shale", Society of Core Analysts, SCA2013-018, Sep. 2013, pp. 1-12.
(Continued)

*Primary Examiner* — Reena Aurora
(74) *Attorney, Agent, or Firm* — Cameron R. Sneddon

(57) ABSTRACT

A method for testing an unconventional core sample is provided. The method involves loading the unconventional core sample into a sample holder and introducing fluid into the sample holder at an elevated pressure such that fluid is injected into the internal pore space of the unconventional core sample in order to resaturate the unconventional core sample with the fluid, wherein the fluid is selected from the
(Continued)

group including a hydrocarbon fluid and a water-based formation fluid. An apparatus and a system used in combination with the method are also provided.

18 Claims, 14 Drawing Sheets

(58) Field of Classification Search
USPC .......................................................... 324/309
See application file for complete search history.

(56) References Cited

U.S. PATENT DOCUMENTS

| | | | |
|---|---|---|---|
| 5,299,453 | A | 4/1994 | Sprunt et al. |
| 8,857,243 | B2* | 10/2014 | Valenza, II .......... G01N 15/088 73/38 |
| 2012/0273193 | A1 | 11/2012 | Sen et al. |
| 2013/0057277 | A1 | 3/2013 | Zielinskl et al. |
| 2013/0113480 | A1 | 5/2013 | Kadayam Viswanathan et al. |
| 2013/0257424 | A1 | 10/2013 | Holland et al. |
| 2013/0261979 | A1 | 10/2013 | Al-Muthana et al. |
| 2014/0002081 | A1 | 1/2014 | Mitchell et al. |

FOREIGN PATENT DOCUMENTS

| | | |
|---|---|---|
| WO | WO2013148516 A1 | 10/2013 |
| WO | WO2013170060 A1 | 11/2013 |

OTHER PUBLICATIONS

Jiang et al., "Integrated Petrophysical Interpretation of Eagle Ford Shale with 1-D and 2-D Nuclear Magnetic Resonance (NMR)", Society of Petrophysicists and Well Log Analysts, Jun. 22-26, 2013 (22 pages).
Rylander et al., "NMR T2 Distributions in the Eagle Ford Shale: Reflections on Pore size", Society of Petroleum Engineers SPE164554, The Woodlands, TX, USA, Apr. 10-12, 2013 (15 pages).
Kausik et al., "NMR Petrophysics for Tight Oil Shale enabled by Core Resaturation", SCA2014-073, presented at the International Symposium of the Society of Core Analysts held in Avignon, France, Sep. 8-11, 2014, (6 pages)
Handwerger et al., "Methods Improve Shale Core Analysis", Reporter, Dec. 2012 (8 pages).
Kausik et al., "NMR Petrophysics for Tight Oil Shale enabled by Core Resaturation", SCA2014-A048 (1 page).
Valori et al., Down-Hole Wettability Estimation Workflow using T1/T2 Ratio (7 pages).
Freedman et al., "Fluid Characterization using Nuclear Magnetic Resonance Logging," Petrophysics, vol. 45, No. 3, May-Jun. 2004, pp. 241-250.
Kausik R., Cao Minh C., Zielinski L., Vissapragada B., Akkurt R., Song Y.-Q., Liu C., Jones S., Blair E., "Characterization of Gas Dynamics in Kerogen Nanopores by NMR", SPE147198, (2011).
Hook P., Fairhurst D., Rylander E., Badry R., Bachman N.H., Crary S., "Improved Precision Magnetic Resonance, Acquisition: Application to Shale Evaluation", SPE146883, (2011).
Cao Minh C., Crary S., Zielinski L., Liu C.B., Jones S., Jacobsen S., "2D-NMR Applications in Unconventional Reservoirs", SPE161578, Oct. 30-Nov. 1, 2012 (18 pages).
Straley C., Rossini D, Vinegar H., Tutunjian P., Morriss C., "Core Analysis by Low-Field NMR", The Log Analyst, Mar.-Apr. 1997, 38, No. 2, p. 84-94.
Alizadeh et al., "Flow Rate Effect on Two-Phase Relative Permeability in Iranian Carbornate Rocks", SPE Middle East Oil and Gas show and Conference, vol. 1, Mar. 11, 2007, pp. 217-222.
Yang et al., "Determination of Residual Oil Distribution during Waterflooding in Tight Oil Formations with NMR Relaxometry Measurements", Energy & Fuels, vol. 27, No. 10, Oct. 17, 2013, pp. 5750-5756.
Hurlimann et al., "Diffusion-relaxation distribution functions of sedimentary rocks in different saturation states", Magnetic Resonance Imaging, Elsevier Science, Tarrytown, NY, US, vol. 21, No. 3-4, Apr. 2003, pp. 305-310.
International Search Report and Written Opinion issued in the Related PCT Application PCT/US2015/012136, dated Apr. 23, 2015 (12 pages).
International Preliminary Report on patentability issued in the Related PCT Application PCT/US2015/012136, dated Jul. 26, 2016 (8 pages).
Extended European Search Report issued in the related EP application 15739776.1, dated Nov. 14, 2017 (9 pages).
International Search Report and Written Opinion issued in the Related PCT Application PCT/US2015/011812, dated Apr. 27, 2015 (15 pages).
International Preliminary Report on Patentability issued in the Related PCT Application PCT/US2015/011812, dated Jul. 26, 2016 (15 pages).

* cited by examiner

WORKFLOW FOR RESATURATION AND ANALYSIS OF UNCONVENTIONAL CORE SAMPLES

CROSS-REFERENCE TO RELATED APPLICATIONS

The present application claims priority from U.S. Provisional Application 61/931,378, filed on Jan. 24, 2014, and U.S. Provisional Application 62/005,075, filed May 30, 2014, both of which are hereby incorporated herein by reference in their entireties.

BACKGROUND

Field

The subject disclosure relates generally to re-saturation of unconventional core samples and analysis of such re-saturated unconventional core samples.

Description of Related Art

The petrophysical analysis of an unconventional core sample can be impeded because the majority of the producible hydrocarbons (and water) that are initially in such unconventional core sample escape from the unconventional core sample in the process of bringing the unconventional core sample from the downhole location where it was obtained to the surface. Routine analysis of conventional core samples includes core cleaning and re-saturation procedures, but for unconventional core samples, no methodology exists.

Economic production from a tight hydrocarbon reservoir is often accomplished by positioning horizontal wells in the reservoir that allows for effective stimulation by hydraulic fracturing. The position of such horizontal wells is often identified using logging and core data acquired from vertical wells that traverse the reservoir. Some of the notable factors that drive successful production from such tight hydrocarbon reservoirs include petrophysical properties, such as porosity, permeability, wettability, hydrocarbon saturation, and pore pressure. Other factors include geomechanical properties such as hydraulic fracture surface area and fracture conductivity. Therefore, accurate measurement of such petrophysical properties may improve performance from tight hydrocarbon reservoirs.

Nuclear magnetic resonance (NMR) core analysis applications have been shown to be useful for the characterization of fluids in shale formations. For example, an understanding of the NMR relaxation and diffusion properties of bound water and gas in gas shale samples has resulted in new methodologies for logging and interpretation in these reservoirs. Recently, interest has shifted to tight hydrocarbon reservoirs because of improvements in technology that make production from such tight hydrocarbon reservoirs economically viable. Laboratory NMR core analysis experiments have been attempted in combination with other methods, such as tight rock analysis (TRA) and mercury injection capillary pressure (MICP), to better characterize the rock from tight hydrocarbon reservoirs.

BRIEF SUMMARY

One drawback of the aforementioned core analysis methodologies is the loss or depletion of formation fluids, including producible hydrocarbons, from the unconventional core sample during its transportation from the downhole location where it was obtained to the surface. The loss of formation fluids from the unconventional core sample may result in measurements taken on the unconventional core sample being non-representative of the formation from which it was obtained. Notwithstanding the foregoing, one direct application of measurements taken on a depleted unconventional core sample is that the porosity difference between the depleted unconventional core sample and log porosities can be used as a proxy for the movable fluid fraction in the tight hydrocarbon reservoir.

However, to accurately analyze an unconventional core sample at its in-situ condition, the unconventional core sample can be resaturated with formation fluids that were in the unconventional core sample in-situ, i.e., in the unconventional core sample while it was downhole in the formation from which it was obtained. One challenge encountered when resaturating an unconventional core sample is the high capillary pressure of the core sample due to the presence of relatively small pores. Therefore, routine core resaturation methods at low pressures, such as centrifuge-based techniques used for conventional cores, are inadequate to introduce the formation fluid into the small pores of the unconventional core sample.

The present disclosure provides an apparatus and workflow to effectively resaturate an unconventional core sample with formation fluid as well as analyze the resaturated core sample in order to accurately determine representative properties of the unconventional core sample. The apparatus and workflow can include i) resaturating the unconventional core sample with formation fluids (such as a hydrocarbon fluid or water-based formation fluid) at high pressures that are at or near in-situ conditions, (ii) petrophysical analysis (such as two-dimensional (2D) NMR $T_1$-$T_2$ experiments) that are particularly adapted to resaturated core samples, and (iii) a demonstration of how such petrophysical analysis can be used to characterize relevant properties of the resaturated core sample as well as the reservoir rock of the tight hydrocarbon reservoir from which the resaturated core sample was obtained.

In at least one aspect, this disclosure relates to an apparatus and methods for resaturating an unconventional core sample with formation fluids (such as a hydrocarbon fluid or water-based formation fluid) and performing one or more petrophysical analyses on the resaturated unconventional core sample to obtain physical properties of the resaturated unconventional core sample. The resaturated unconventional core sample is representative of the reservoir rock from which the unconventional core sample was obtained; therefore, information obtained from the analysis of the resaturated unconventional core sample can be used to characterize properties of the reservoir rock in the formation of interest (the tight hydrocarbon reservoir).

In one embodiment, the disclosure relates to a method for testing an unconventional core sample that involves loading the unconventional core sample into a sample holder and introducing fluid into the sample holder at an elevated pressure such that fluid is injected into the internal pore space of the unconventional core sample in order to resaturate the unconventional core sample with the fluid. The fluid is selected from the group including a hydrocarbon fluid and a water-based formation fluid. The elevated pressure can be selected according to at least one of pore size of the unconventional core sample and capillary pressure of the unconventional core sample. The elevated pressure can be at least 2,000 psig (140.6 kg/square cm gauge).

The method can further include performing analysis on the unconventional core sample resaturated with fluid at the elevated pressure, wherein the analysis derives physical properties of the reservoir rock from which the unconventional core sample was obtained.

In one embodiment, the fluid injected into the unconventional core sample can be a hydrocarbon fluid, and the physical properties derived from the analysis can include at least one property that particularly relates to organic pore space of the reservoir rock that holds producible hydrocarbons. The physical properties derived from the analysis can further include at least one property that particularly relates to inorganic pore space of the reservoir rock that holds producible hydrocarbons. The hydrocarbon fluid can be obtained from the reservoir rock from which the unconventional core sample was obtained.

In another embodiment, the fluid injected into the unconventional core sample can be a water-based formation fluid, and the physical properties derived from the analysis include at least one property that particularly relates to inorganic pore space of the reservoir rock that holds producible water-based formation fluid. The water-based formation fluid can be brine having a salinity that matches the salinity of brine held by the reservoir rock from which the unconventional core sample was obtained.

In one embodiment, the analysis of the resaturated core sample can involve multidimensional NMR experiments.

In another aspect, the disclosure relates to a method for testing unconventional core samples involving loading a first unconventional core sample into a sample holder and introducing a hydrocarbon fluid into the sample holder at an elevated pressure such that hydrocarbon fluid is injected into the internal pore space of the first unconventional core sample in order to resaturate the first unconventional core sample with the hydrocarbon fluid. Analysis is performed on the first unconventional core sample resaturated with hydrocarbon fluid at the elevated pressure, wherein the analysis derives physical properties of the reservoir rock from which the first unconventional core sample was obtained, wherein the physical properties derived from the analysis include at least one property that particularly relates to organic pore space of the reservoir rock that holds producible hydrocarbons. The physical properties derived from the analysis performed on the first unconventional core sample further include at least one property that particularly relates to inorganic pore space of the reservoir rock that holds producible hydrocarbons. A second (twin) unconventional core sample is loaded into a sample holder, wherein the second unconventional core sample is obtained from the same reservoir rock as the first unconventional core sample, and a water-based formation fluid is introduced into the sample holder at an elevated pressure such that the water-based formation fluid is injected into the internal pore space of the second unconventional core sample in order to resaturate the second unconventional core sample with the water-based formation fluid. Analysis is performed on the second unconventional core sample resaturated with water-based formation fluid at the elevated pressure, wherein the analysis derives physical properties of the reservoir rock from which the second unconventional core sample was obtained. The physical properties derived from the analysis include at least one property that particularly relates to inorganic pore space of the reservoir rock that holds producible water-based formation fluids.

In one embodiment, the elevated pressure can be selected according to at least one of pore size of the first and second unconventional core samples and capillary pressure of the first and second unconventional core samples. The elevated pressure can be at least 2,000 psig (140.6 kg/square cm gauge).

In one embodiment, the analysis performed on both the first unconventional core sample and the second unconventional core sample can involve multidimensional NMR experiments.

In yet another aspect, the disclosure relates to a method for testing an unconventional core sample involving loading an unconventional core sample into a sample holder and introducing a hydrocarbon fluid into the sample holder at an elevated pressure such that the hydrocarbon fluid is injected into the internal pore space of the unconventional core sample in order to resaturate the unconventional core sample with the hydrocarbon fluid. Analysis is performed on the unconventional core sample resaturated with hydrocarbon fluid at the elevated pressure, wherein the analysis derives physical properties of the reservoir rock from which the unconventional core sample was obtained. The physical properties derived from such analysis include at least one property that particularly relates to organic pore space of the reservoir rock that holds producible hydrocarbons and can include at least one property that particularly relates to inorganic pore space of the reservoir rock that holds producible hydrocarbons.

Subsequent or prior to the resaturation and test of the unconventional core sample with hydrocarbon fluid, water-based formation fluid is introduced into the sample holder at an elevated pressure such that the water-based formation fluid is injected into the internal pore space of such unconventional core sample in order to resaturate the unconventional core sample with the water-based formation fluid. Analysis is performed on the unconventional core sample resaturated with water-based formation fluid at the elevated pressure, wherein the analysis derives physical properties of the reservoir rock from which the unconventional core sample was obtained. The physical properties derived from such analysis include at least one property that particularly relates to inorganic pore space of the reservoir rock that holds producible water-based formation fluids.

In one embodiment, the elevated pressure can be selected according to at least one of pore size of the unconventional core sample and capillary pressure of the unconventional core sample. The elevated pressure can be at least 2,000 psig (140.6 kg/square cm gauge).

In one embodiment, the analysis performed on the unconventional core sample re-saturated with both hydrocarbon fluid and water-based formation fluid can involve multidimensional NMR experiments.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings.

DETAILED DESCRIPTION

As used herein, the term "core sample" means a rock sample obtained downhole from a hydrocarbon reservoir, which is intended to be representative of the rock formation at the downhole location where the rock sample was obtained. The core sample can be cylindrical in shape, and obtained during or after drilling a well through the rock formation. Cores can be full-diameter cores (that is, they are nearly as large in diameter as the drill bit) taken at the time of drilling the zone, or sidewall cores (generally less than 1 inch in diameter) taken after a borehole has been drilled.

As used herein, the term "unconventional core sample" is a core sample obtained from a tight hydrocarbon reservoir.

As used herein, the term "tight hydrocarbon reservoir" is a reservoir containing hydrocarbons (such as oil and/or natural gas) that is formed of relatively impermeable reservoir rock from which hydrocarbon production is difficult. The relative impermeability of the reservoir rock can be caused by smaller grains or matrix between larger grains, or caused by predominant silt-sized or clay-sized grains (as is the case for tight shale reservoirs). Tight hydrocarbon reservoirs can contain oil and/or natural gas as well as water-based formation fluid such as brine in the relatively impermeable reservoir rock.

As used herein, the term "resaturated unconventional core sample" or "resaturated test sample" is an unconventional core sample that is loaded with liquid-phase formation fluid (such as an oil or a water-based formation fluid such as brine) to a state approximating the in-situ conditions of the reservoir rock from which the unconventional core sample was obtained.

As used herein, the term "organic porosity" or "organic pore space" means porosity or pore space defined by organic matter (e.g., organic kerogen) of reservoir rock, the term "inorganic porosity" or "inorganic pore space" means porosity or pore space defined by inorganic matter (i.e., the intraparticle and intergranular pores defined by the minerals of the rock, such as the clays) of reservoir rock, and the term "total porosity" means the sum of both organic porosity and inorganic porosity of the reservoir rock. Note that in shales, organic porosity is often the predominant component of total porosity. Moreover, due to the hydrophobic nature of organic matter, the organic porosity of reservoir rock is in most cases fully occupied by producible hydrocarbons whereas the inorganic porosity of reservoir rock is occupied by water-based formation fluids (such as brines). Therefore, understanding the organic porosity of the reservoir rock can aid in characterizing the total porosity distribution of the reservoir rock and improve understanding of fluid saturation in the reservoir rock.

As used herein, the term "petrophysical properties" means physical and chemical properties of reservoir rock and its hydrocarbon content and non-hydrocarbon content, such as water-based formation fluids.

Figure 1A:
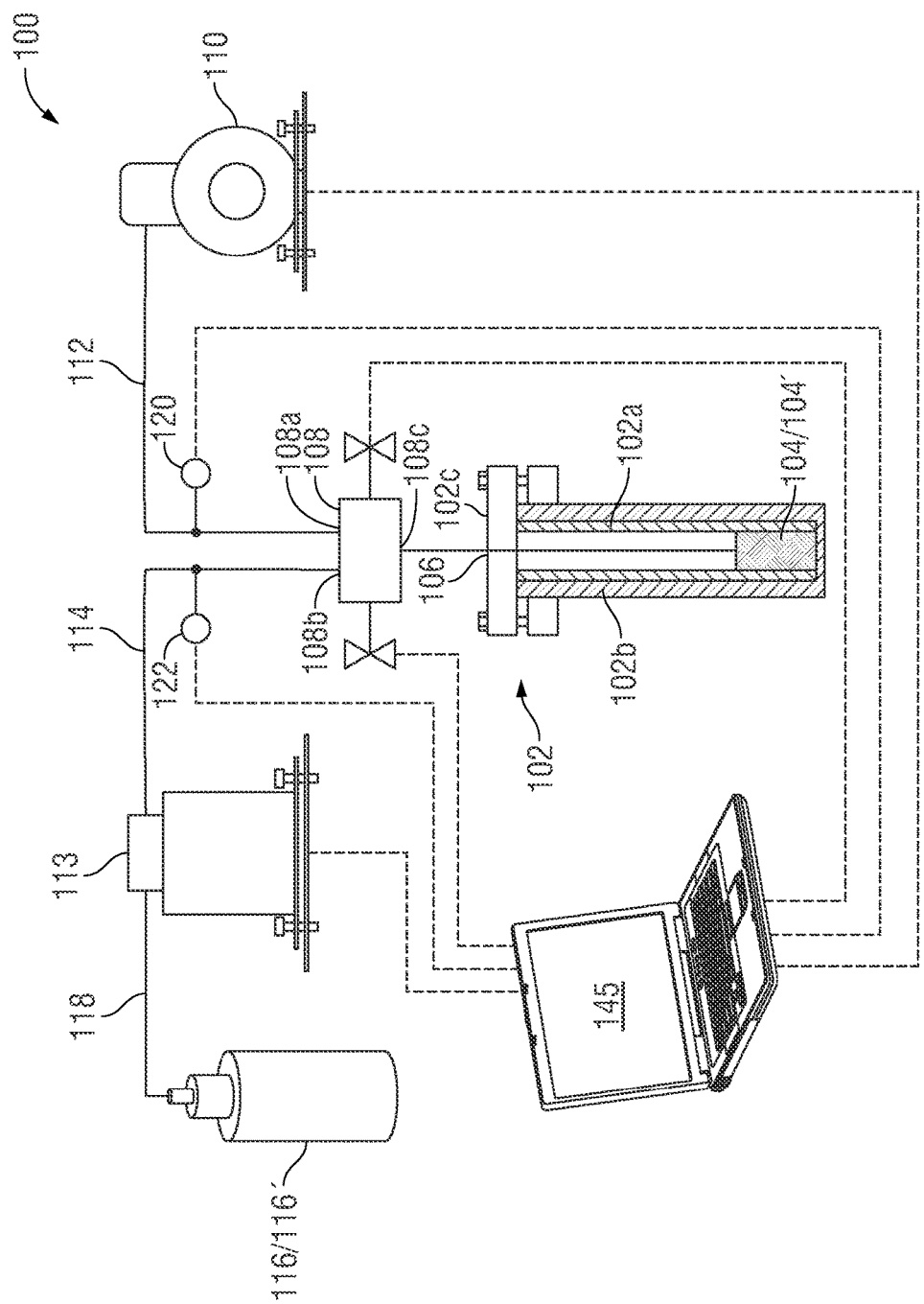
FIG. 1A shows a test apparatus suitable for testing unconventional core samples in accordance with one embodiment of the present disclosure.

FIG. 1A shows an embodiment of a test apparatus 100 in accordance with an aspect of this disclosure. The test apparatus 100 includes a sample holder 102 having an inner sleeve 102a, an outer sleeve 102b, and a flanged lid 102c. The inner sleeve 102a is configured to receive and retain a test sample 104, such as an unconventional core sample as described herein. The flanged lid 102c can be opened to introduce the test sample 104 into the inner sleeve 102a and closed to seal the test sample 104 in the sample holder 102. In one embodiment, the inner sleeve 102a can be constructed from a thermoplastic polymer such as Polyether ether ketone (PEEK), and the outer sleeve 102b can be constructed from fiberglass. The sealed sample holder 102 can be configured to draw fluid (such as air) from the sample holder 102 under negative pressure and to inject the test sample 104 with fluid under positive pressure as part of the workflows described herein. In one embodiment, the sample holder 102 may be capable of being pressurized up to 5,000 psi (351.5 kg/square cm). The lid 102c of the sample holder 102 has a port 106 that is fluidly coupled to a three-way valve 108. The port 106 provides fluid communication between the inside of the inner sleeve 102a (which contains the test sample 104) and the valve 108.

The three-way valve 108 includes three ports 108a, 108b, and 108c. The port 108a is fluidly coupled to a vacuum pump 110 via a vacuum line 112. The vacuum pump 110 can be configured to draw fluid (such as air) from the sample holder 102 under negative pressure. The port 108b is fluidly coupled to a high pressure pump 113 via a high pressure line 114. The high pressure pump 113 is fluidly coupled via a line 118 to a supply of fluid 116 that is to be injected into the test sample 104 for fluid resaturation of the test sample 104 as described herein. In one embodiment, the valve 108 and the high pressure line 114 are supplied by High Pressure Equipment Company of Erie, Pa., USA and rated to at least 30,000 psi (2109 kg/square cm). The port 108c is fluidly coupled to the port 106 of the sample holder 102 such that it is in fluid communication with the inside of the inner sleeve 102a of the sample holder 102.

A first pressure sensor 120 can be fluidly coupled to the vacuum line 112 between the vacuum pump 110 and the valve 108. The first pressure sensor 120 can be configured to monitor the fluid pressure in the vacuum line 112. A second pressure sensor 122 can be fluidly coupled to the high pressure line 114 between the high pressure pump 113 and the valve 108. The second pressure sensor 122 can be configured to monitor the fluid pressure in the high pressure line 114. In one embodiment the first and second pressure sensors 120, 122, the three-way valve 108, the high pressure pump 113, and the vacuum pump 110 are communicatively coupled to a computer system 145 that is constructed to control the operation of those components in accordance with the workflows described below. The three-way valve 108 is selectively operated to switch between placing the vacuum pump 110 or the high pressure pump 113 in fluid communication with the inside of the inner sleeve 102a (which contains the test sample 104) of the sample holder 102.

In one embodiment, the sample holder 102 can be made of non-magnetic material that does not interfere with obtaining NMR measurements of the test sample 104 that is placed in the sample holder 102. Also, the sample holder 102 can be configured such that the test sample 104 having been resaturated with fluid can be tested using NMR measurements while the test sample 104 is disposed in the sample holder 102 under high pressure conditions, such as at high pressures that simulate the in-situ conditions of the reservoir rock from which the test sample 104 was obtained.

The controller and/or computer system 145 can include control logic that interfaces to the pumps 110 and 113 via wired or wireless signal paths therebetween for control of the operation of the pumps 110 and 113, that interfaces to the electrically-controlled valve 108 via wired or wireless signal paths therebetween for control of the operation of the valve 108, and that interfaces to the pressure sensors 120, 122, via wired or wireless signal paths therebetween. The control logic of the controller and/or computer system 145 (which can be embodied in software that is loaded from persistent memory and executed in the computing platform of the computer system 145) is configured to control the different parts of the test apparatus 100 to carry out a sequence of operations (workflow) to resaturate the test sample 104 as described below. The control logic can be configured by user input or a testing script or other suitable data structure, which is used to configure the controller or the computer system 145 in order to carry out control operations that are part of the workflow as described herein. For example, the user input or the testing script or other suitable data structure can specify parameters (such as pressures, flow rates, etc.) for such control operations of the workflow.

An embodiment of a workflow using the test apparatus 100 of FIG. 1A to resaturate a test sample 104 and a twin test sample 104' will now be described with respect to FIG. 1B. In this example, the test sample 104 is an unconventional core sample obtained from a tight hydrocarbon reservoir containing oil, and the twin test sample 104' is another unconventional core sample obtained from the same tight hydrocarbon reservoir.

In block 201, the test sample 104 is placed into the inner sleeve 102a of the sample holder 102 and the flanged lid 102c is closed to seal the test sample 104 in the sample holder 102 such that the port 108c of the valve 108 is in fluid communication with the inside of the inner sleeve 102a of the sample holder 102.

In block 203, the valve 108 is configured so that the vacuum pump 110 is in fluid communication with the inside of the inner sleeve 102a (which contains the test sample 104) of the sample holder 102 and the high pressure pump 113 is not in fluid communication with the inside of the inner sleeve 102a. With the valve 108 so configured, the vacuum pump 110 is operated for a time sufficient to evacuate any air inside the inner sleeve 102a of the sample holder 102. This air is discharged through line 112 and through the vacuum pump 110. To avoid drawing residual oil from the test sample 104 the applied vacuum is kept relatively weak and is applied for a relatively short time of about one hour or less.

In block 205, the valve 108 is reconfigured (i.e., switched) so that the high pressure pump 113 is in fluid communication with the inside of the inner sleeve 102a (which contains the test sample 104) of the sample holder 102 and the vacuum pump 110 is not in fluid communication with the inside of the inner sleeve 102a. With the valve 108 so configured, the high pressure pump 113 is operated to introduce a liquid-phase hydrocarbon fluid (i.e., oil) 116 to the inside of the inner sleeve 102a of the sample holder 102 at high pressure. In one embodiment, the oil 116 is the same oil (or similar oil in terms of viscosity and density) as that contained in the reservoir rock from which the test sample 104 was obtained, and the high pressure of the introduced oil 116 is controlled based on pore size distribution and the capillary pressure calculated for the test sample 104. The high pressure is set based on the permeability and size of the test sample 104. In such high pressure condition, the oil 116 is injected into the test sample 104 such that the test sample 104 is resaturated with the oil 116 at or near in-situ conditions. The high pressure of the oil 116 supplied to the sample holder 102 can be monitored using the second pressure sensor 122 and such pressure can be controlled to maintain a relatively constant fluid pressure level based on the monitored pressure.

After the test sample 104 is resaturated with the oil at high pressure, in block 207 petrophysical analysis can be carried out on the resaturated test sample 104 contained in the sample holder 102 at the high pressure conditions of the resaturation operations of block 205. Such petrophysical analysis characterizes petrophysical properties that characterize the oil-containing pore space of the reservoir rock from which the test sample 104 was obtained.
Such petrophysical properties can include porosity, saturation, wettability (such as an Amott-Harvey index or USBM index), pore pressure, and/or other useful properties for the pore space of the reservoir rock that is injected with oil by the high pressure resaturation operations of block 205. These petrophysical properties, which collectively can be referred to as "injected oil" properties, can be equated to petrophysical properties of the reservoir rock that contains producible oil, which can be referred to as "movable oil" properties. Such movable oil properties can include porosity, saturation, wettability (such as an Amott-Harvey index or USBM index), pore pressure, and/or other useful properties for the pore space of the reservoir rock that contains producible oil. Geomechanical and geochemical properties of the reservoir rock may also be derived from the analysis.

Note that the petrophysical analysis of block 207 can be configured to measure one or more injected oil properties specific to the organic pore space of the reservoir rock of the resaturated core sample as well as one or more injected oil properties specific to the inorganic pore space of the reservoir rock of the resaturated core sample. In this case, the injected oil porosity (which can be equated to movable oil porosity) can possibly be derived from the injected oil porosity for the organic pore space of the reservoir rock (or possibly from the sum of the injected oil porosity for the organic pore space of the reservoir rock and the injected oil porosity (or some part thereof that accounts for producible water) for the inorganic pore space of the reservoir rock. Similarly, the injected oil saturation (which can equated to movable oil saturation) can possibly be derived from the injected oil saturation for the organic pore space of the reservoir rock (or possibly from the sum of the injected oil saturation for the organic pore space of the reservoir rock and the injected oil saturation (or some part thereof that accounts for producible water) for the inorganic pore space of the reservoir rock). Similarly, the measure of wettability of the reservoir rock that contains producible oil can possibly be derived from the wettability of the organic pore space of the reservoir rock that contains producible oil (or possibly based on a function of the wettability of the organic pore space of the reservoir rock that contains producible oil and the wettability of the inorganic pore space of the reservoir rock that contains producible oil). Similarly, the measure of pore pressure of the reservoir rock that contains producible oil can possibly be derived from the pore pressure of the organic pore space of the reservoir rock that contains producible oil (or possibly based on a function of the pore pressure of the organic pore space of the reservoir rock that contains producible oil and the pore pressure of the inorganic pore space of the reservoir rock that contains producible oil). Also note that the pore space of the oil resaturated core sample can hold non-movable or bound hydrocarbons (such as bitumen) as well as non-movable or bound water-based formation fluids. In this case, the petrophysical analysis can be configured to separate out the contribution of this pore space from the movable oil properties measured by the petrophysical analysis of block 207. In one non-limiting example, the petrophysical analysis of block 207 can include multidimensional NMR experiments as described below.

After the analysis of block 207, the high pressure conditions of the test sample 104 as contained in the sample holder 102 can be decreased to ambient pressure, the flanged lid 102c of the sample holder 102 can be opened, and the test sample 104 can be removed from the sample holder 102, if need be.

In block 209, the twin test sample 104' is placed in the inner sleeve 102a of the sample holder 102 (or into another like sample holder) and the flanged lid 102c is closed to seal the twin test sample 104' in the sample holder 102 such that the port 108c of the valve 108 is in fluid communication with the inside of the inner sleeve 102a of the sample holder 102.

In block 211, the valve 108 is configured so that the vacuum pump 110 is in fluid communication with the inside of the inner sleeve 102a (which contains the twin test sample 104') of the sample holder 102 and the high pressure pump 113 is not in fluid communication with the inside of the inner sleeve 102a. With the valve 108 so configured, the vacuum pump 110 is operated for a time sufficient to evacuate any air inside the inner sleeve 102a of the sample holder 102. This air is discharged through line 112 and through the vacuum pump 110.

In block 213, the valve 108 is reconfigured (i.e., switched) so that high pressure pump 113 is in fluid communication with the inside of the inner sleeve 102a (which contains the twin test sample 104') of the sample holder 102 and the vacuum pump 110 is not in fluid communication with the inside of the inner sleeve 102a. The high pressure pump 113 is operated to introduce a water-based formation fluid 116' to the inside of the inner sleeve 102a of the sample holder 102 at high pressure. In one embodiment, the water-based formation fluid 116' is the same brine fluid (or brine fluid with similar salinity) as that contained in the reservoir rock from which the twin test sample 104' was obtained, and the high pressure of the introduced water-based formation fluid 116' is controlled based on pore size distribution and the capillary pressure calculated for the twin test sample 104'. In such high pressure condition, the water-based formation fluid 116' is injected into the twin test sample 104' such that the twin test sample 104' is resaturated with the water-based formation fluid 116' at or near in-situ conditions. The high pressure of the water-based formation fluid 116' supplied to the sample holder can be monitored using the second pressure sensor 122 and such pressure can be controlled to maintain a relatively constant fluid pressure level based on the monitored pressure.

After the twin test sample 104' is resaturated with the water-based formation fluid 116' at high pressure, in block 215 petrophysical analysis can be carried out on the resaturated twin test sample 104' contained in the sample holder 102 at the high pressure conditions of the resaturation operations of block 213. Such petrophysical analysis characterizes petrophysical properties that characterize the water-based-fluid-containing pore space of the reservoir rock from which the twin test sample 104' was obtained. Such petrophysical properties can include porosity, saturation, wettability (such as an Amott-Harvey index or USBM index), pore pressure, and/or other useful properties for the pore space of the reservoir rock that is injected with the water-based formation fluid by the high pressure resaturation operations of block 213. These petrophysical properties, which collectively can be referred to as "injected water" properties, can be equated to petrophysical properties of the reservoir rock that contains producible water, which can be referred to as "movable water" properties. Such movable water properties can include porosity, saturation, wettability (such as an Amott-Harvey index or USBM index), pore pressure, and/or other useful properties for the pore space of the reservoir rock that contains producible water. Geomechanical and geochemical properties of the reservoir rock may also be derived from the analysis.

Note that the pore space of the water resaturated core sample can hold non-movable or bound hydrocarbons (such as bitumen) as well as non-movable or bound water-based formation fluids. In this case, the petrophysical analysis can be configured to separate out the contribution of this pore space from the movable water properties measured by the petrophysical analysis of block 215. In one non-limiting example, the petrophysical analysis of block 215 can include multidimensional NMR experiments as described below.

After the analysis of block 215, the high pressure conditions of the twin test sample 104' as contained in the sample holder 102 can be decreased to ambient pressure, the flanged lid 102c of the sample holder 102 can be opened, and the twin test sample 104' can be removed from the sample holder 102, if need be.

Additional analysis can possibly be performed using the results of block 207 and/or block 215. For example, a predicted water-cut during production can be calculated from the ratio of movable water saturation derived in block 215 to the movable oil saturation derived in block 207. In another example, the total porosity of movable fluids of the reservoir rock (sometimes referred to as "total effective porosity") can be calculated as the sum of movable oil porosity of block 207 and the movable water porosity of block 215. This total effective porosity can be compared to gas porosity of the reservoir rock measured by pulsed-decay and/or crushed rock analysis.

It is also contemplated that the workflow can involve testing of a native (or "as-is") unconventional core sample obtained from the same tight hydrocarbon reservoir where the native core sample is not resaturated with formation fluids. In this case, the petrophysical analysis of block 207 and/or block 215 can employ the results of such testing on the native unconventional core sample in deriving the injected oil properties and/or injected water properties of the reservoir rock.

Another embodiment of a workflow using the apparatus 100 of FIG. 1A to resaturate a test sample 104 will now be described with respect to FIG. 1C. In this example, the test sample 104 is an unconventional core sample obtained from a tight hydrocarbon reservoir containing oil, such as a tight oil shale formation.

In block 301, the test sample 104 is placed into the inner sleeve 102a of the sample holder 102 and the flanged lid 102c is closed to seal the test sample 104 in the sample holder 102 such that the port 108c of the valve 108 is in fluid communication with the inside of the inner sleeve 102a of the sample holder 102.

In block 303, the valve 108 is configured so that the vacuum pump 110 is in fluid communication with the inside of the inner sleeve 102a (which contains the test sample 104) of the sample holder 102 and the high pressure pump 113 is not in fluid communication with the inside of the inner sleeve 102a. With the valve 108 so configured, the vacuum pump 110 is operated for a time sufficient to evacuate any air inside the inner sleeve 102a of the sample holder 102. This air is discharged through line 112 and through the vacuum pump 110.

In block 305, the valve 108 is reconfigured (i.e., switched) so that the high pressure pump 113 is in fluid communication with the inside of the inner sleeve 102a (which contains the test sample 104) of the sample holder 102 and the vacuum pump 110 is not in fluid communication with the inside of the inner sleeve 102a. With the valve 108 so configured, the high pressure pump 113 is operated to introduce a liquid-phase oil 116 to the inside of the inner sleeve 102a of the sample holder 102 at high pressure. In one embodiment, the oil 116 is the same oil (or an oil of similar viscosity and density) as that contained in the reservoir rock from which the test sample 104 was obtained, and the high pressure of the introduced oil 116 is controlled based on pore size distribution and the capillary pressure calculated for the test sample. In such high pressure condition, the oil 116 is injected into the test sample 104 such that the test sample 104 is resaturated with the oil 116 at or near in-situ conditions. The high pressure of the oil 116 supplied to the sample holder 102 can be monitored using the second pressure sensor 122 and such pressure can be controlled to maintain a relatively constant fluid pressure level based on the monitored pressure.

After the test sample 104 is resaturated with the oil at high pressure, in block 307 petrophysical analysis can be carried out on the resaturated test sample 104 contained in the sample holder 102 at the high pressure conditions of the resaturation operations of block 305. Such petrophysical analysis characterizes petrophysical properties that characterize the oil-containing pore space of the reservoir rock from which the test sample 104 was obtained.

Such petrophysical properties can include porosity, saturation, wettability (such as an Amott-Harvey index or USBM index), pore pressure, and/or other useful properties for the pore space of the reservoir rock that is injected with oil by the high pressure resaturation operations of block 305. These petrophysical properties, which collectively can be referred to as "injected oil" properties, can be equated to petrophysical properties of the reservoir rock that contains producible oil, which can be referred to as "movable oil" properties. Such movable oil properties can include porosity, saturation, wettability (such as an Amott-Harvey index or USBM index), pore pressure, and/or other useful properties for the pore space of the reservoir rock that contains producible oil. Geomechanical and geochemical properties of the reservoir rock may also be derived from the analysis.

Note that the petrophysical analysis of block 307 can be configured to measure one or more injected oil properties specific to the organic pore space of the reservoir rock of the resaturated core sample as well one or more injected oil properties specific to the inorganic pore space of the reservoir rock of the resaturated core sample. In this case, the injected oil porosity (which can be equated to movable oil porosity) can possibly be derived from the injected oil porosity for the organic pore space of the reservoir rock (or possibly from the sum of the injected oil porosity for the organic pore space of the reservoir rock and the injected oil porosity (or some part thereof that accounts for producible water) for the inorganic pore space of the reservoir rock). Similarly, the injected oil saturation (which can equated to movable oil saturation) can possibly be derived from the injected oil saturation for the organic pore space of the reservoir rock (or possibly from the sum of the injected oil saturation for the organic pore space of the reservoir rock and the injected oil saturation (or some part thereof that accounts for producible water) for the inorganic pore space of the reservoir rock). Similarly, the measure of wettability of the reservoir rock that contains producible oil can possibly be derived from the wettability of the organic pore space of the reservoir rock that contains producible oil (or possibly based on a function of the wettability of the organic pore space of the reservoir rock that contains producible oil and the wettability of the inorganic pore space of the reservoir rock that contains producible oil). Similarly, the measure of pore pressure of the reservoir rock that contains producible oil can possibly be derived from the pore pressure of the organic pore space of the reservoir rock that contains producible oil (or possibly based on a function of the pore pressure of the organic pore space of the reservoir rock that contains producible oil and the pore pressure of the inorganic pore space of the reservoir rock that contains producible oil). Also note that the pore space of the oil resaturated core sample can hold non-movable or bound hydrocarbons (such as bitumen) as well as non-movable or bound water-based formation fluids. In this case, the petrophysical analysis can be configured to separate out the contribution of this pore space from the movable oil properties measured by the petrophysical analysis of block 307. In one non-limiting example, the petrophysical analysis of block 307 can include multidimensional NMR experiments as described below.

In block 309, the valve 108 is reconfigured so that the vacuum pump 110 is in fluid communication with the inside of the inner sleeve 102*a* and the high pressure pump 113 is not in fluid communication with the inside of the inner sleeve 102*a*. With the valve 108 so configured, the vacuum pump 110 can be operated to depressurize the sample holder 102 and remove excess oil from the inside of the inner sleeve 102*a* of the sample holder 102.

In block 311, the valve 108 is reconfigured (i.e., switched) so that the high pressure pump 113 is in fluid communication with the inside of the inner sleeve 102*a* (which contains the test sample 104) of the sample holder 102. The high pressure pump 113 is operated to introduce a water-based formation fluid 116' to the inside of the inner sleeve 102*a* of the sample holder 102 at high pressure. In one embodiment, the water-based formation fluid 116' is the same brine fluid (or brine fluid with similar salinity) as that contained in the reservoir rock from which the test sample 104 was obtained, and the high pressure of the introduced water-based formation fluid 116' is controlled based on pore size distribution and the capillary pressure calculated for the test sample. In such high pressure condition, the water-based formation fluid 116' is injected into the test sample 104 such that the test sample 104 is resaturated with the water-based formation fluid 116' at or near in-situ conditions. The high pressure of the water-based formation fluid 116' supplied to the sample holder 102 can be monitored using the second pressure sensor 122 and such pressure can be controlled to maintain a relatively constant fluid pressure level based on the monitored pressure.

After the test sample 104 is resaturated with the water-based formation fluid 116' at high pressure, in block 313 petrophysical analysis can be carried out on the resaturated test sample 104 contained in the sample holder 102 at the high pressure conditions of the resaturation operations of block 311. Such petrophysical analysis characterizes petrophysical properties that characterize the water-based-formation-fluid-containing pore space of the reservoir rock from which the test sample 104 was obtained. Such petrophysical properties can include porosity, saturation, wettability (such as an Amott-Harvey index or USBM index), pore pressure, and/or other useful properties for the pore space of the reservoir rock that is injected with the water-based formation fluid by the high pressure resaturation operations of block 311. These petrophysical properties, which collectively can be referred to as "injected water" properties, can be equated to petrophysical properties of the reservoir rock that contains producible water, which can be referred to as "movable water" properties. Such movable water properties can include porosity, saturation, wettability (such as an Amott-Harvey index or USBM index), pore pressure, and/or other useful properties for the pore space of the reservoir rock that contains producible water. Geomechanical and geochemical properties of the reservoir rock may also be derived from the analysis.

Note that the pore space of the water resaturated core sample can hold non-movable or bound hydrocarbons (such as bitumen) as well as non-movable or bound water-based formation fluids. In this case, the petrophysical analysis can be configured to separate out the contribution of this pore space from the movable water properties measured by the petrophysical analysis of block 313. In one non-limiting example, the petrophysical analysis of block 313 can include multidimensional NMR experiments as described below.

After the analysis of block 313, the high pressure conditions of the test sample 104 as contained in the sample holder 102 can be decreased to ambient pressure, the flanged lid 102*c* of the sample holder 102 can be opened, and the test sample 104 can be removed from the sample holder 102, if need be.

Additional analysis can possibly be performed using the results of block 307 and/or block 313. For example, a predicted water-cut during production can be calculated from the ratio of movable water saturation derived in block 313 to the movable oil saturation derived in block 307. In another example, the total porosity of movable fluids of the reservoir rock (sometimes referred to as "total effective porosity") can be calculated as the sum of movable oil porosity derived in block 307 and the movable water porosity derived in block 313. This total porosity can be compared to gas porosity of the reservoir rock measured by pulsed-decay and/or crushed rock analysis. Other properties and useful information that characterize the reservoir rock and the producible fluids contained therein can possibly be calculated from the petrophysical properties derived in block 307 and/or block 313.

It is also contemplated that the workflow can involve testing of a native (or "as-is") unconventional core sample obtained from the same tight hydrocarbon reservoir where the native core sample is not resaturated with formation fluids. In this case, the petrophysical analysis of block 307 and/or block 313 can employ the results of such testing on the native unconventional core sample in deriving the injected oil properties and/or injected water properties of the reservoir rock.

Figure 1B:
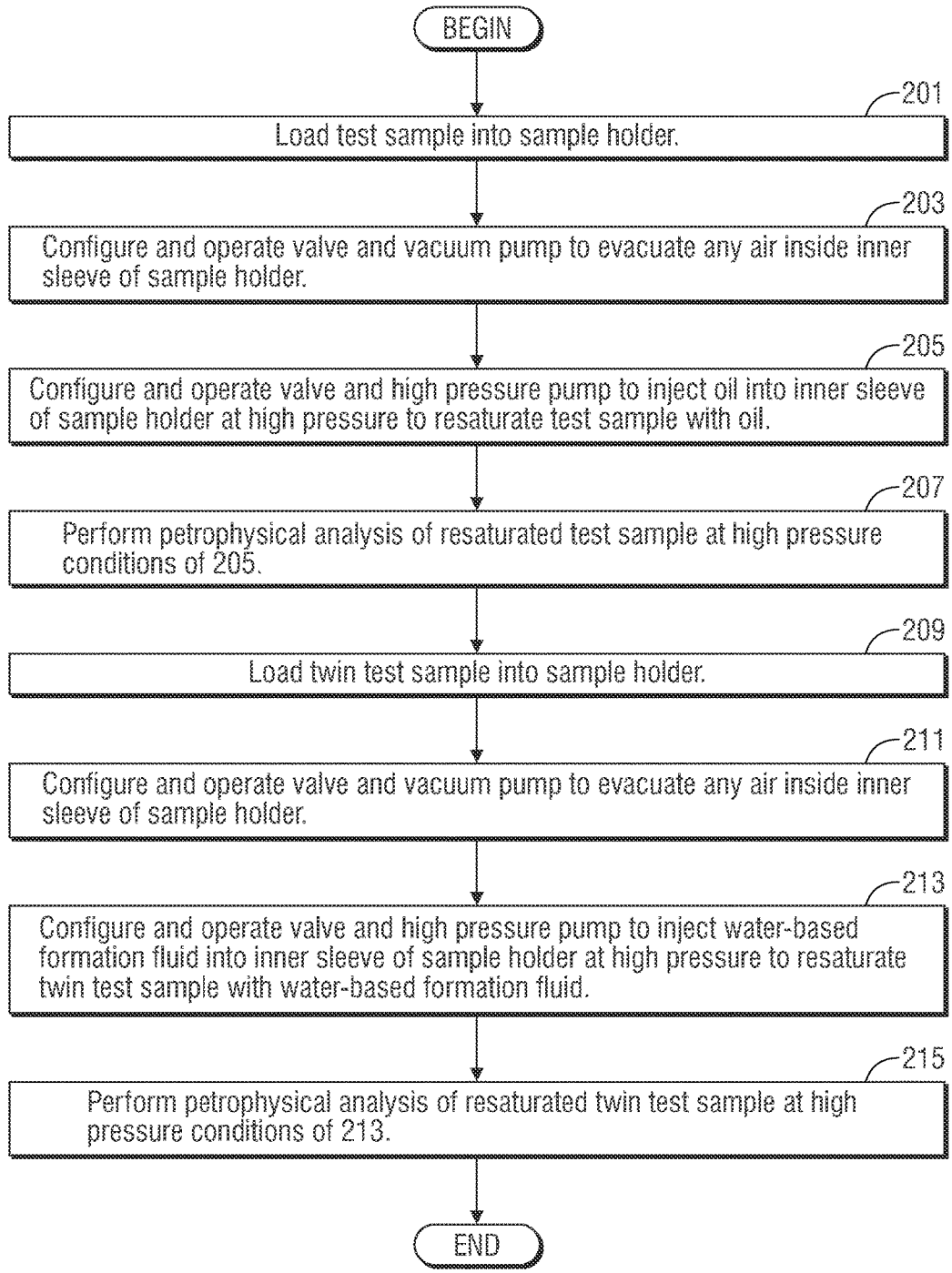
FIG. 1B is a flow chart of an exemplary workflow using the test apparatus of FIG. 1A to resaturate two twin unconventional core samples with an oil and water-based formation fluid, respectively, and test the resaturated unconventional core samples in accordance with one embodiment of the present disclosure.
Figure 1C:
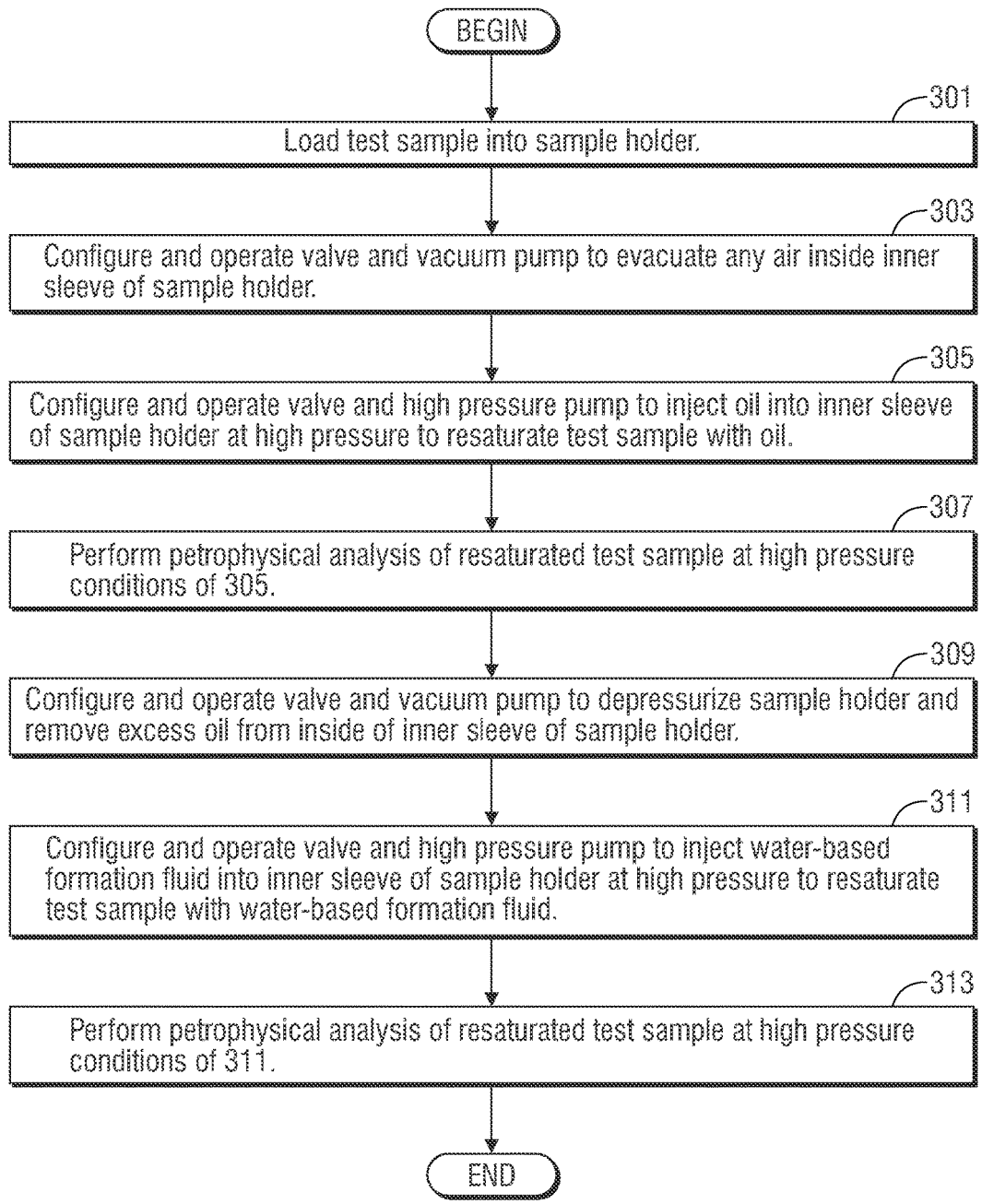
FIG. 1C is a flow chart of an exemplary workflow using the test apparatus of FIG. 1A to resaturate an unconventional core sample with both an oil and water-based formation fluid and test the resaturated unconventional core sample in accordance with another embodiment of the present disclosure.

Note that in the workflow of FIG. 1B, twin test samples are resaturated with oil and water-based formation fluid, respectively, for separate petrophysical analysis of the resaturated twin test samples. In the workflow of FIG. 1C, the same test sample is resaturated with oil followed by water-based formation fluid in a sequential manner for sequential petrophysical analysis of the resaturated test sample. In an alternate embodiment, the workflow of FIG. 1C can be adapted such that the same test sample is resaturated with water-based formation fluid followed by oil in a sequential manner for sequential petrophysical analysis of the resaturated test sample. In this manner, the sequential order of the resaturation and associated petrophysical analysis for the oil and the water-based formation fluid is reversed.

The petrophysical analysis of the resaturated test samples can include multidimensional NMR experiments. In these multidimensional NMR experiments, multidimensional NMR data ($T_1$, $T_2$, D) may be electronically acquired using a rock core analyzer (such as the GeoSpec2 analyzer available from Oxford Instruments plc of Abingdon, UK) at a resonance frequency of about 2 MHz, which, preferably, is also the same frequency as a wellbore logging tool used downhole in the wellbore. The multidimensional NMR experiments can be made at ambient temperature (22° C.) using echo times (TE) of 100 μseconds. In an alternate embodiment, the multidimensional NMR experiments can be made at other temperatures, such as high temperatures corresponding to the in-situ reservoir conditions of the test sample, and at different magnetic field strengths or frequencies. The multidimensional NMR data ($T_1$, $T_2$, and D) can be derived by subtracting the raw NMR signal measured on the native unconventional core sample from the raw NMR signal measured on the respective resaturated core sample followed by inversion using an inverse Laplace transform.

In one embodiment, the multidimensional NMR experiments of one or more resaturated test samples loaded with oil (e.g., blocks 207 or 307) can be used to obtain a $T_2$ distribution of the resaturated test sample(s) loaded with oil. In this case, the area under such $T_2$ distribution less the area under the $T_2$ distribution of the native sample can be integrated (e.g., summed) to derive a measure of injected oil porosity of the resaturated test sample(s), which is similar in some respects to the derivation of total porosity based on $T_2$ distributions described in "Fluid Characterization using Nuclear Magnetic Resonance Logging," R. Freedman and N. Heaton, *Petrophysics*, Vol. 45, No. 3, May-June 2004, pp. 241-250. In this case, the injected oil porosity of the resaturated test sample(s) can be equated to movable oil porosity of the reservoir rock of the test sample(s) and thus can be interpreted as a representative measure of porosity (pore space) that contains movable (producible) oil for the reservoir rock from which the oil resaturated test sample(s) was obtained. The $T_2$ distribution of the resaturated test samples less the $T_2$ distribution of the native sample, when integrated, yields the amount of oil injected into the sample. This represents the amount of movable oil that existed in the formation but was lost in the process of bringing the cores to the surface. The wettability (such as an Amott-Harvey index or USBM index) of the pore space that contains movable oil can be derived by an empirical correlation to the multidimensional NMR data, such as a correlation to the average $T_1/T_2$ ratio for NMR $T_1$-$T_2$ data that particularly relates to the injected oil pore space of the reservoir rock (and does not particularly relate to the pore space of the reservoir rock that contains producible water).

Similarly, the multidimensional NMR experiments of one or more resaturated test samples loaded with water-based formation fluid (e.g., blocks 215 or 313) can be used to obtain a $T_2$ distribution of the resaturated test sample loaded with water-based formation fluid. In this case, the area under such $T_2$ distribution less the area under the $T_2$ distribution of the native sample can be integrated (e.g., summed) to derive a measure of the injected water porosity of the resaturated test sample(s). In this case, the injected water porosity of the resaturated test sample(s) can be equated to movable water porosity of the reservoir rock of the test sample(s) and thus can be interpreted as a representative measure of porosity (pore space) that contains movable (producible) water for the reservoir rock from which the water resaturated test sample(s) was obtained. The $T_2$ distribution of the resaturated test samples less the $T_2$ distribution of the native sample, when integrated, yields the amount of water injected into the sample. This represents the amount of movable water that existed in the formation but was lost in the process of bringing the cores to the surface. The wettability (such as an Amott-Harvey index or USBM index) of the pore space that contains movable water can be derived by an empirical correlation to the multidimensional NMR data, such as a correlation to the average $T_1/T_2$ ratio for NMR $T_1$-$T_2$ data that particularly relates to the injected water pore space of the reservoir rock (and does not particularly relate to the pore space of the reservoir rock that contains producible oil).

A quality check can be performed by summing the injected oil and injected water porosities of the resaturated test sample(s) to approximate total porosity of the reservoir rock of the resaturated test sample(s) and then comparing such approximation of total porosity of the reservoir rock to gas porosity and/or Brunauer-Emmett-Teller (BET) porosity of the same reservoir rock, which can be measured utilizing other well-known techniques. Note that the BET porosity provides precise specific surface area evaluation of materials by nitrogen multilayer adsorption measured as a function of relative pressure using a fully automated analyser. The BET porosity measurement encompasses external area and pore area evaluations to determine the total specific surface area in $m^2/g$ yielding important information in studying the effects of surface porosity and particle size in many applications.

The workflows as described herein have been validated by resaturating core-like samples of porous VYCOR® glass available from Corning Incorporated of Corning, N.Y., USA, whose porosity simulates unconventional core samples. Specifically, cylindrical VYCOR® glass, having a 4 nm unimodal pore size, was cut into samples having dimensions of 3.5 cm by 0.6 cm. Using the test apparatus 100 of FIG. 1A and, in accordance with the workflow described above with respect to FIG. 1B, two VYCOR® porous glass rod samples were subject to vacuum evacuation for two hours and combusted to 800° C. prior to being resaturated with dodecane (an oil) at a pressure of 2,000 psi (140.6 kg/square cm) for a period of 48 hours while being held in respective sample holders. Also, two other VYCOR® porous glass rod samples were subject to vacuum evacuation for two hours and saturated with water at a pressure of 2,000 psi (140.6 kg/square cm) for a period of 48 hours while being held in respective sample holders. Each saturated porous glass rod sample was tested using multidimensional NMR experiments while being held in their respective sample holders at their respective 2,000 psi (140.6 kg/square cm) fluid pressures. $T_1$ and $T_2$ distributions were obtained for each saturated porous glass rod sample. Furthermore, bulk water was introduced into a sample holder and subjected to the same multidimensional NMR experiments. $T_1$ and $T_2$ distributions were obtained for the bulk water. Similarly, bulk dodecane was introduced into a sample holder 102 and subjected to the same multidimensional NMR experiments. $T_1$ and $T_2$ distributions were obtained for the bulk dodecane.

Figure 2:
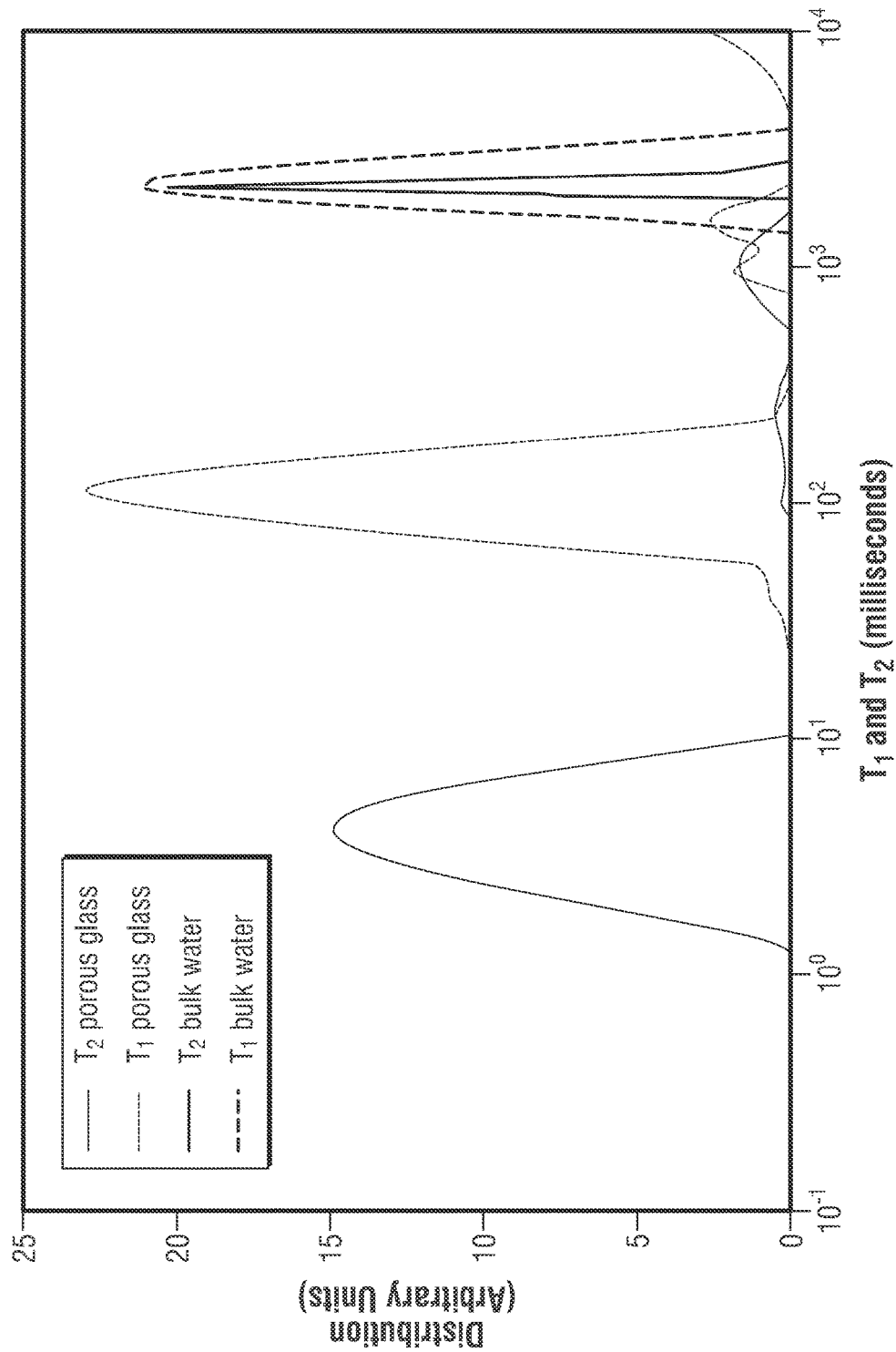
FIG. 2 shows $T_1$ and $T_2$ distributions of NMR data produced by multidimensional NMR experiments on a porous glass sample resaturated with water and corresponding multidimensional NMR experiments on bulk water.

FIG. 2 shows the $T_1$ and $T_2$ distributions for bulk water and for the porous glass rod samples that were saturated with water. Note that there is a marked shift in the $T_1$ and $T_2$ distributions between the bulk water and the porous glass rod samples that were saturated with water, indicating that the water is disposed in the pores of the porous glass rod samples. The area under the $T_2$ distribution of the porous glass rod samples can be integrated to derive the water-injected porosity of the porous glass rod samples, which is analogous to the inorganic porosity of the resaturated unconventional core samples tested by the workflows described herein.

Figure 3:
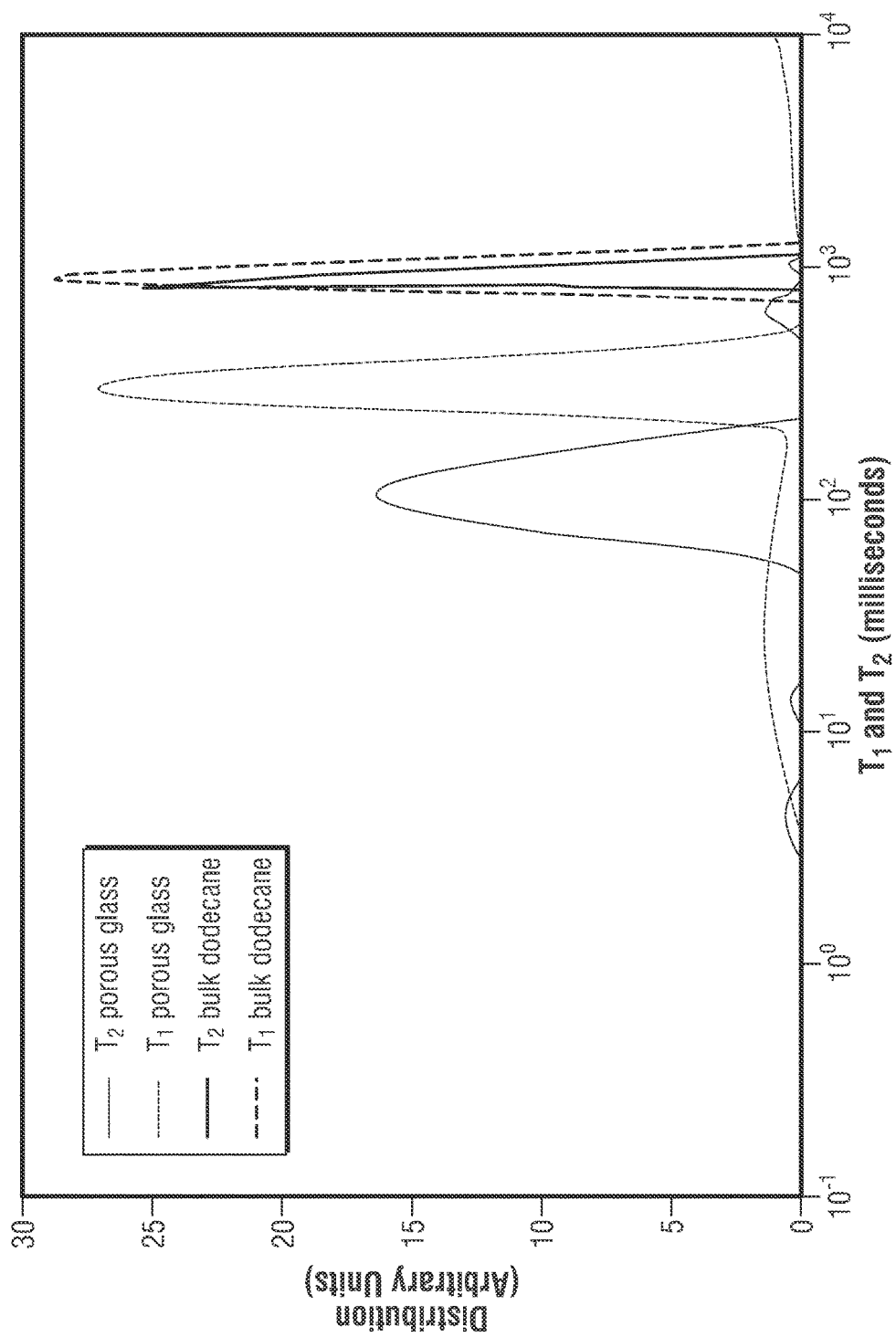
FIG. 3 shows $T_1$ and $T_2$ distributions of NMR data produced by multidimensional NMR experiments on a porous glass sample resaturated with dodecane and corresponding multidimensional NMR experiments on bulk dodecane.

FIG. 3 shows $T_1$ and $T_2$ distributions for bulk dodecane and for the porous glass rod samples that were saturated with dodecane. Note that there is a marked shift in the $T_1$ and $T_2$ distributions between the bulk dodecane and the porous glass rod samples that were saturated with dodecane, indicating that the dodecane is disposed in the pores of the porous glass rod samples. The area under the $T_2$ distribution of the porous glass rod samples can be integrated to derive the dodecane-injected porosity of the porous glass rod samples, which is analogous to the organic porosity of the resaturated unconventional core samples tested by the workflows described herein.

The oil injected porosity and the water injected porosity can be summed to approximate a total porosity as shown in Table 1. The total porosity can be compared with the gas porosity and/or BET porosity for the respective porous glass rod samples as shown in Table 1, which shows an acceptable match between the total porosity measured by the NMR experiments and the conventional gas porosity and BET porosity measurements.

More specifically, the total porosity of the saturated porous glass rod samples slightly exceeds the gas porosity (by 0.93% to 9.35%) and the BET porosity (by 4.11% to 8.97%). This indicates that all 4 nm pores of the saturated porous glass rod samples were completely saturated, thereby validating the resaturation workflow described above using the apparatus 100 of FIG. 1A. Also, as complete dodecane saturation of the extremely hydrophilic glass pores of 4 nm size was successful, this validates the application of the resaturation workflow for unconventional core samples.

TABLE 1

| Sample | Gas Porosity | BET Porosity | Total Porosity by NMR - grain volume |
|---|---|---|---|
| VYCOR ® 1 | 31.0 | 31.8 | 33.9 |
| VYCOR ® 2 | 30.9 | 31.6 | 32.9 |
| VYCOR ® 3 | 32.0 | 30.0 | 32.3 |
| VYCOR ® 4 | 31.0 | 30.1 | 32.8 |

Figure 4:
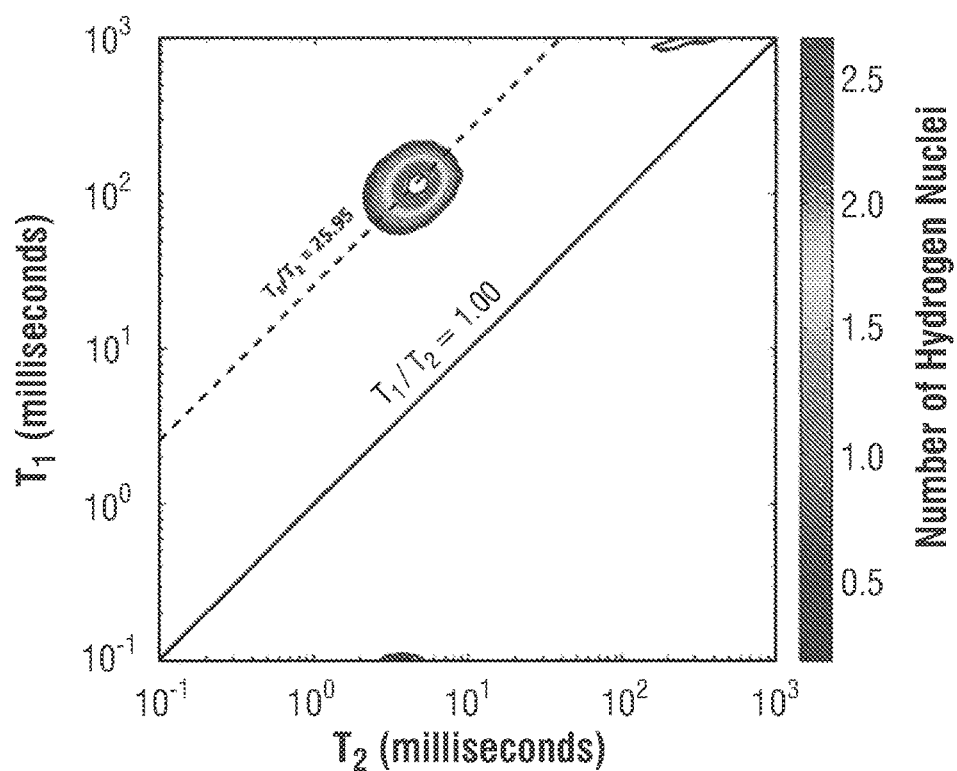
FIG. 4 shows a $T_1$-$T_2$ map of NMR data produced by multidimensional NMR experiments on a porous glass sample resaturated with water.
Figure 5:
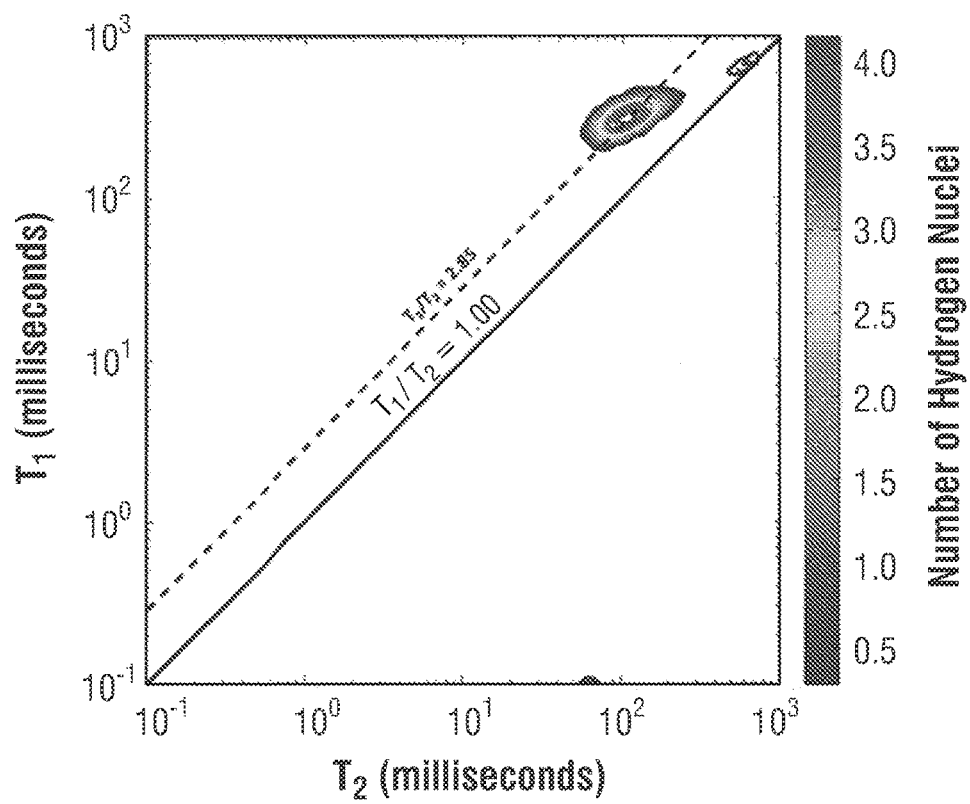
FIG. 5 shows a $T_1$-$T_2$ map of NMR data produced by multidimensional NMR experiments on a porous glass sample resaturated with dodecane.

Other observations from the data in FIGS. 2 and 3 can be made. For example, as shown in FIG. 2, the $T_1$ value of the water saturated porous glass rod samples is about 100 ms compared to the $T_1$ value of the bulk water sample which is about 3,000 ms, while the $T_2$ value of the water saturated porous glass rod samples VYCOR® glass sample is about 4 ms compared to $T_2$ value of the bulk water sample which is about 3,000 ms, resulting in a $T_1/T_2$ ratio of about 26, as shown in FIG. 4. As shown in FIG. 3, the $T_1$ value of the dodecane saturated porous glass rod samples is about 285 ms compared to the $T_1$ value of the bulk dodecane sample which is about 2,000 ms, while the $T_2$ value of the dodecane saturated porous glass rod samples is about 100 ms compared to the $T_2$ value of the bulk dodecane sample which is about 2,000 ms, resulting in a $T_1/T_2$ ratio of about 2.85, as shown in FIG. 5. It is understood that the increase in the $T_1/T_2$ ratios is due to the slowing down of fluid motion at the pore surfaces in the porous glass rod samples. The $T_1/T_2$ ratio is especially high for the case of the water as the porous silicon oxide glass is highly hydrophilic and is therefore strongly water wetting. The $T_1/T_2$ values for oil are only slightly increased from the bulk value due to the moderate fluid slowdown at the pore surfaces.

In another aspect, the workflows as described herein have been validated by resaturating portions of a solid cylindrical unconventional core sample obtained from the lower Eagle Ford formation in Texas, USA. In this example, the unconventional core sample was used to form end trims of irregular shapes and broken to cross-sectional dimensions of 1 mm to 2 mm to increase surface to volume ratios for fluid resaturation. The unconventional core sample was chosen to avoid high clay streaks. Bulk density measurements were made on the solid cylindrical unconventional core sample and were used to determine bulk volumes of the end trims. The bulk densities of both the solid cylindrical unconventional core sample and the end trims were similar, indicating good core preservation over the 18 month period after the unconventional core sample was recovered from the lower Eagle Ford formation. A first end trim (a test sample that is to remain un-saturated in its as-received or native state) was not resaturated with fluids at all. A second end trim (a test sample to be resaturated with oil) was resaturated with formation oil obtained from the lower Eagle Ford formation using the apparatus 100 of FIG. 1A, as described above with respect to the workflow of FIG. 1B. A third end trim (a twin test sample to be resaturated with water-based formation fluid) was resaturated with brine having the same salinity as the brine from the lower Eagle Ford formation using the apparatus 100 of FIG. 1A, as described above with respect to the workflow of FIG. 1B.

The first end trim (the native test sample), the second end trim (the resaturated test sample loaded with oil), and the third end trim (the resaturated test sample loaded with brine) were separately tested using multidimensional NMR experiments as follows. Two-dimensional NMR data was acquired with 24 log-spaced inversion recovery steps ranging from 0.2 ms to 1 second with echo times (TE) of 100 µseconds and processed by subtracting the raw NMR signal measured on the native test sample from the raw NMR signal measured on the respective resaturated core sample followed by inversion using a fast inverse Laplace transform, which included the Mellin transform for 1D data. The NMR data obtained for each of the three end trims was used to plot 2D NMR $T_1$-$T_2$ maps.

Figure 6:
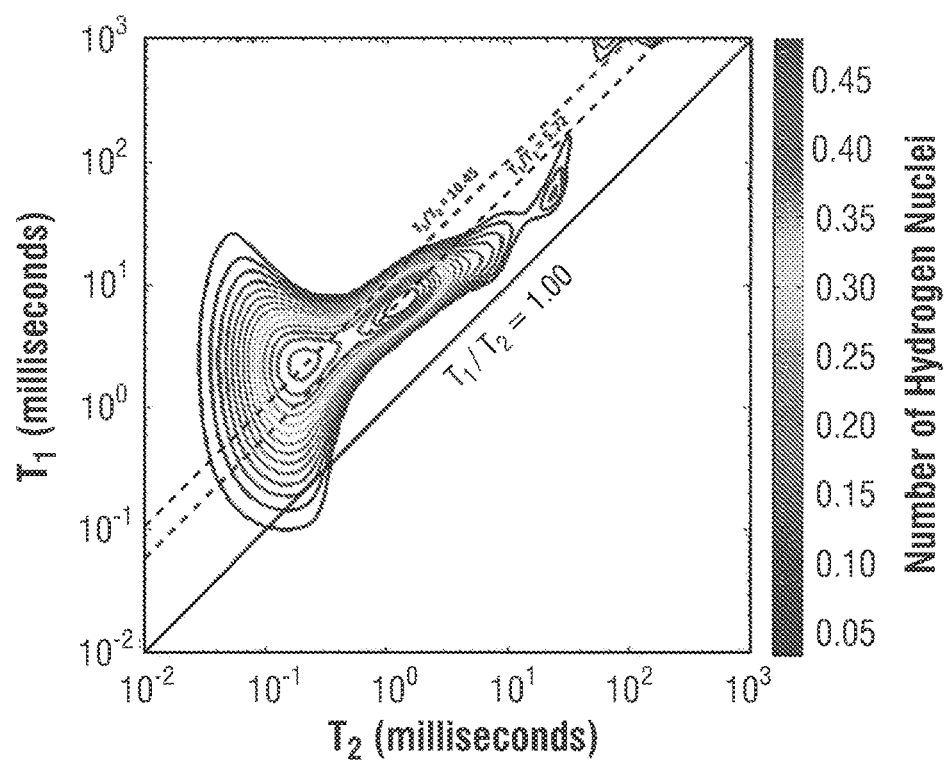
FIG. 6 shows a $T_1$-$T_2$ map of NMR data produced by multidimensional NMR experiments on a first end trim of an unconventional core sample where the first end trim is not resaturated with fluid, but is in its native as-received state.

FIG. 6 shows a plot of a 2D NMR $T_1$-$T_2$ map of the NMR data acquired for the first end trim that was not resaturated with fluid. The 2D NMR $T_1$-$T_2$ map of FIG. 6 reveals peaks at $T_1/T_2$ ratios of 10.45 and 5.72. These peaks correspond to residual matter as the movable fluids escape during retrieval of the unconventional core sample. A first peak with a $T_1/T_2$ ratio between 6 and 16 (generally around 10.45) and a $T_2$ value less than 1.5 ms (generally between 0.1 and 1 ms) corresponds to bitumen as confirmed by laboratory experiments. Clay-bound water overlaps with this NMR signal and is not clearly differentiated from the bitumen due to the low resolution in the maps at these relatively short relaxation times. In other words, bound water with comparable $T_2$, but much smaller $T_1/T_2$ ratios, is not well separated from bitumen due to a lack of resolution at short relaxation times. A second peak is shown in FIG. 6 having a $T_1/T_2$ ratio of 5.72, and a $T_2$ value between 1 ms and 10 ms. This second peak corresponds to residual oil in the organic pore space (organic porosity) of the first end trim. This residual oil contained in the organic porosity (organic pore space) of the reservoir rock is movable (producible) fluid. Laboratory core analysis, in combination with formation logging, can be used for its characterization. A third peak is shown in FIG. 6 in the region of $T_2$s between 10 ms and 100 ms. This third peak corresponds to movable (producible) fluids, such as residual oil and residual water-based formation fluid, in the inorganic pore space (the inorganic porosity) of the first end trim.

Figure 7:
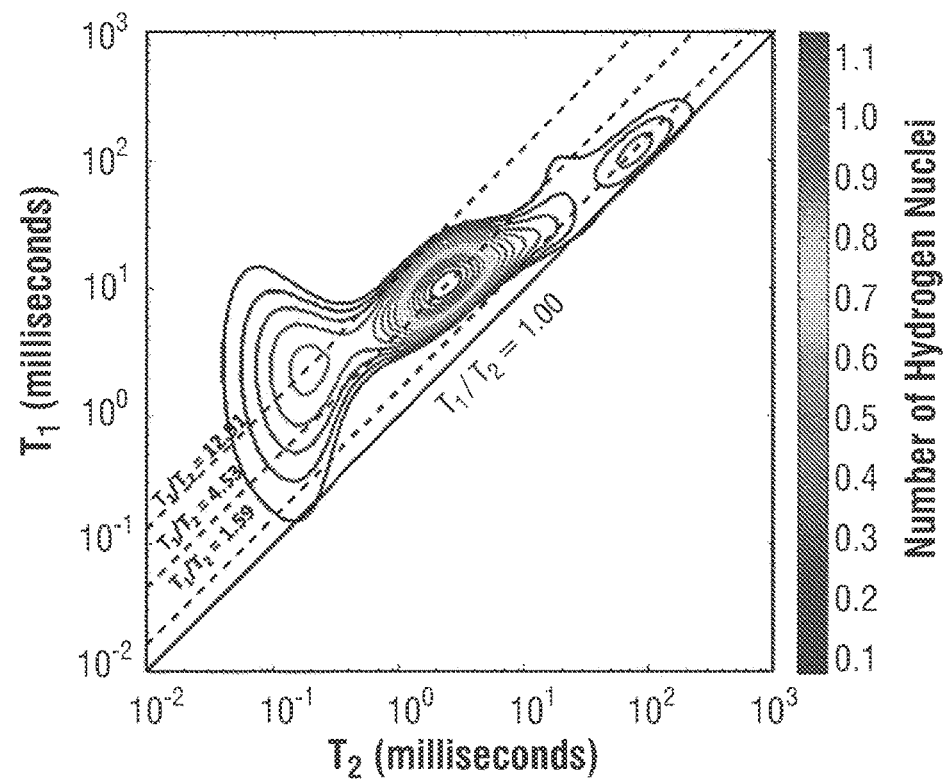
FIG. 7 shows a $T_1$-$T_2$ map of NMR data produced by multidimensional NMR experiments on a second end trim of the unconventional core sample where the second end trim is resaturated with formation oil.

FIG. 7 shows a plot of a 2D NMR $T_1$-$T_2$ map of the NMR data acquired for the second end trim that is resaturated with oil from the lower Eagle Ford formation. The 2D NMR $T_1$-$T_2$ map of FIG. 7 shows three peaks at $T_1/T_2$ ratios of 12.81, 4.53, and 1.59, respectively. The first two peaks at the shorter relaxation times are similar to those of the non-resaturated end trim of FIG. 6. However, in comparison to the map shown in FIG. 6, the map of FIG. 7 shows that for the test sample resaturated with oil, there is a large increase in the $T_2$ distributions for $T_1/T_2$ ratios between 3 and 8 (more specifically around 5) and a $T_2$ value between 0.5 ms and 10 ms. This region corresponds to movable (producible) oil contained in the organic pore space (organic porosity) of the reservoir rock. The organic pore space (organic porosity) of the reservoir rock that contains the oil can also be identified from the 1D $T_2$ distributions shown in FIG. 8 of the second end trim (labeled "Resaturated with oil") as compared to those of the first end trim (labeled "Native state"). Note that FIG. 7 also shows a third peak at a $T_1/T_2$ ratio between 1 and 3 (more specifically around 1.59) with $T_2$s generally above 10 ms. This third peak corresponds to the movable (producible) oil contained in the inorganic pore space (inorganic porosity) of the reservoir rock.

Thus, from the 2D NMR plots shown in FIGS. 6 and 7, different regions of some relevant petrophysical properties can be visualized based on an identification of organic and inorganic porosity regimes. For example, the plots show that oil is producible from two environments. The first environment corresponds to the second peak in FIG. 7 which particularly relates to oil contained in the organic porosity of the reservoir rock. This first environment is represented by $T_2$s from 0.5 ms to 10 ms and with $T_1/T_2$ ratios of about 3 to 8. The second environment corresponds to the third peak in FIG. 7 which particularly relates to oil contained in inorganic porosity of the reservoir rock. This second environment is represented by $T_2$s generally above 10 ms and with $T_1/T_2$ ratios of about 1 to 3 (at elevated temperature (approximately 104° C.) the $T_2$ cutoff increases compared to that at ambient temperature and ranges from 3 ms to 200 ms depending on rock type and the $T_1/T_2$ ratio ranges between 1 and 3). Therefore, the analysis of the NMR data for the three end trim samples can be used to characterize the producible oil contained in both the organic porosity and the inorganic porosity of the reservoir rock. Specifically, the two components are well separated, which allows for the determination of suitable filter parameters ($T_2$ cutoff values and corresponding $T_1/T_2$ ratios) for the NMR data in order to measure the producible oil contained in both the organic porosity and the inorganic porosity of the reservoir rock for accurate oil recovery estimates, which in turn can aid in well completion methodologies and production predictions.

Figure 8:
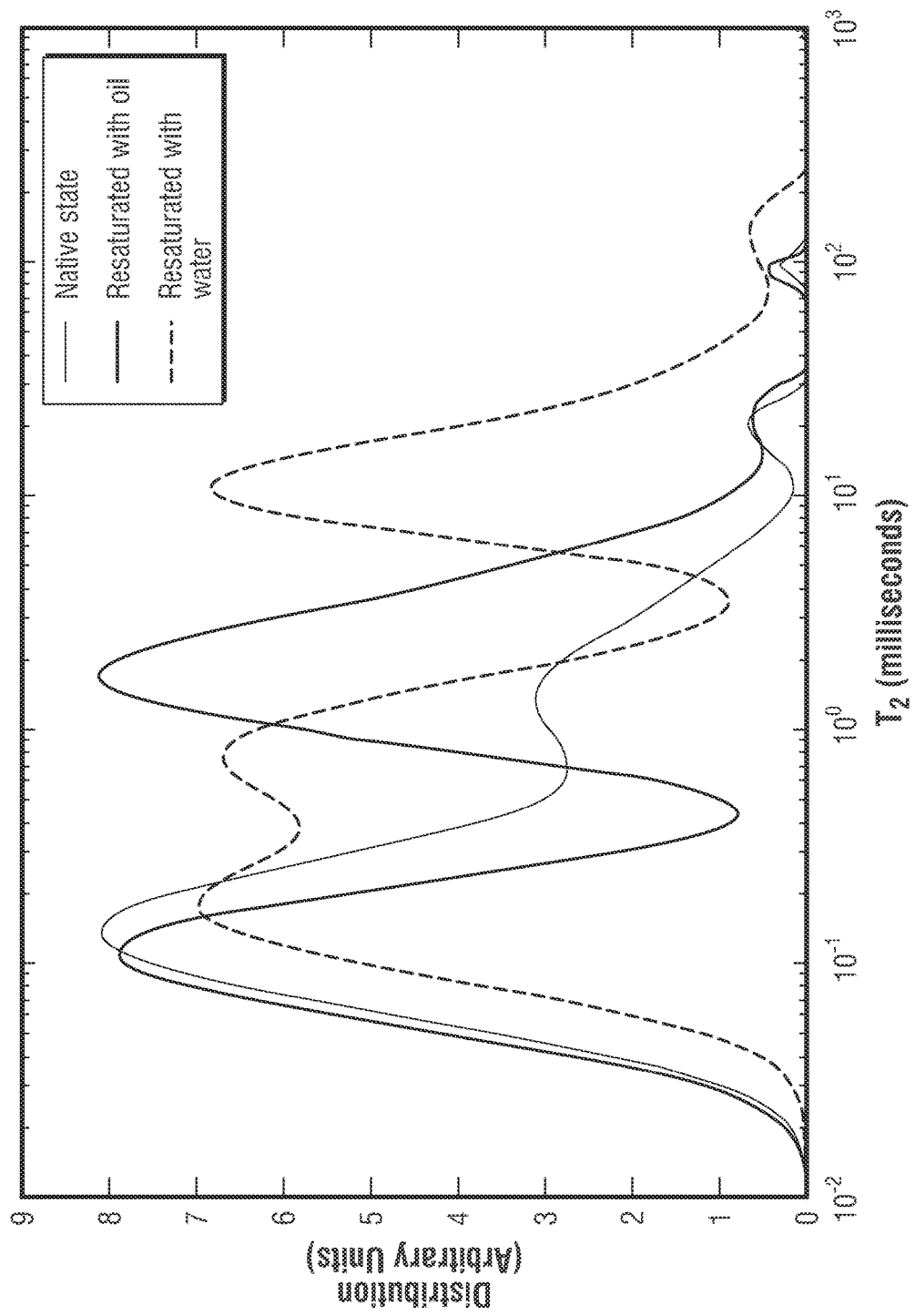
FIG. 8 shows one-dimensional (1D) $T_2$ distributions of NMR data produced by multidimensional NMR experiments on three end trims obtained from the same unconventional core sample, where the first end trim is not resaturated with fluid (it is in its native as-received state), where the second end trim is resaturated with formation oil, and where the third end trim is resaturated with formation water (brine).
Figure 9:
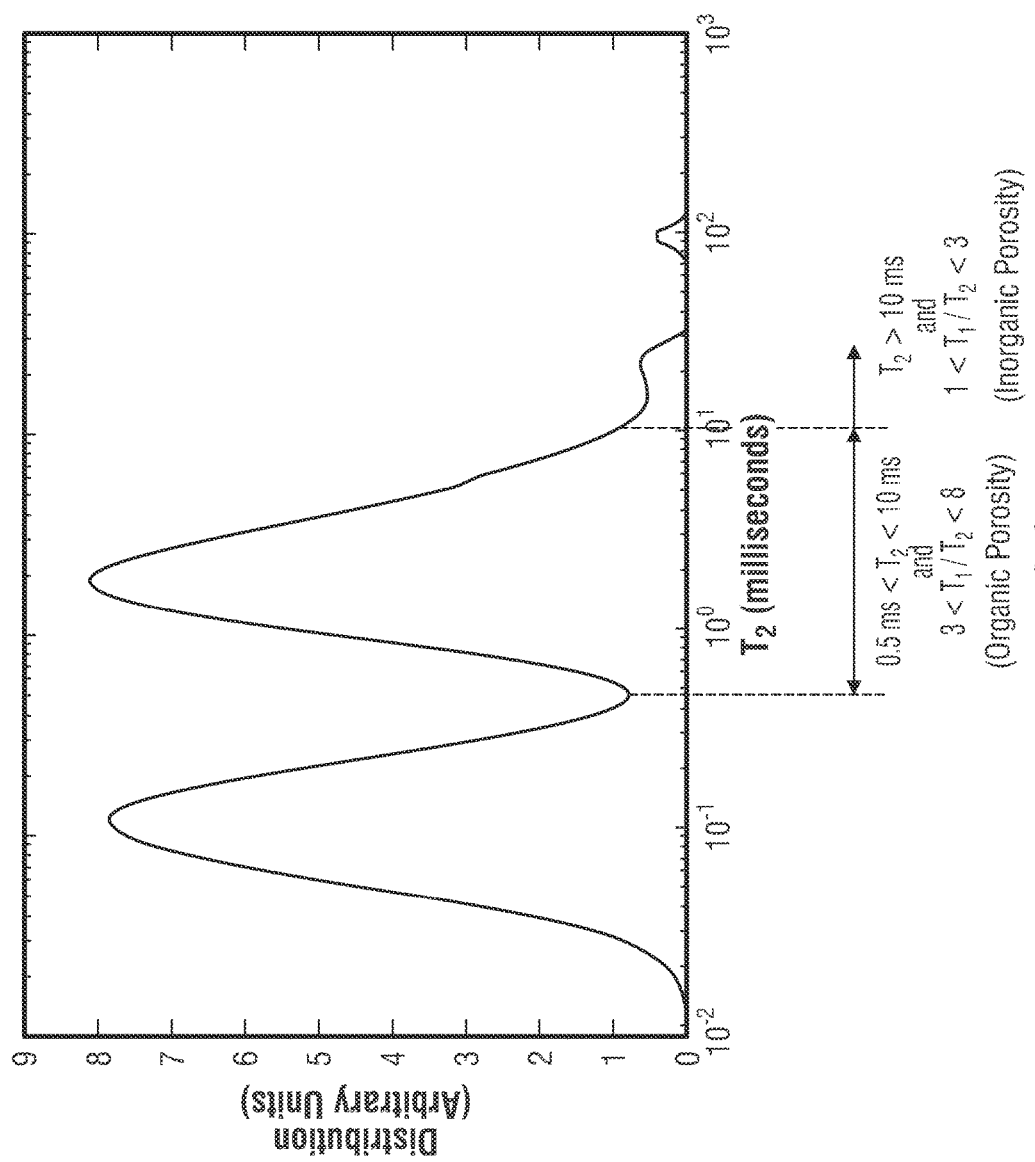
FIG. 9 shows one of the 1D $T_2$ distributions of FIG. 8, which is part of the NMR data produced by multidimensional NMR experiments on the second end trim resaturated with formation oil. The 1D $T_2$ distribution is depicted in conjunction with markings showing two regimes (and corresponding filter parameters), where one regime pertains to the organic porosity of the reservoir rock from which the second end trim was obtained that contains producible oil, and where the other regime pertains to the inorganic porosity of the reservoir rock from which the second end trim was obtained that contains producible oil.
Figure 10:
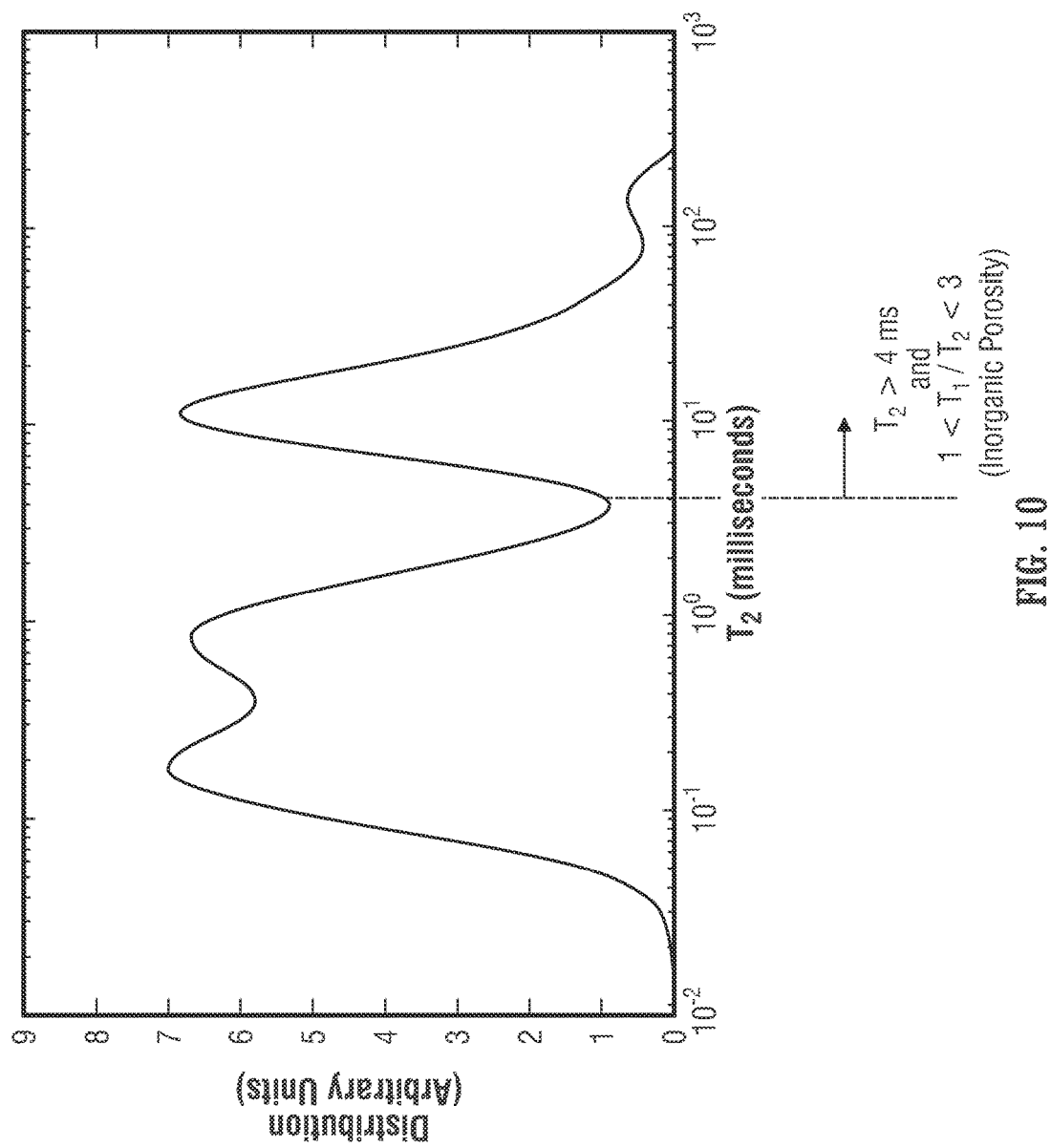
FIG. 10 shows one of the 1D $T_2$ distributions of FIG. 8, which is part of the NMR data produced by multidimensional NMR experiments on the third end trim resaturated with formation water (brine). The 1D $T_2$ distribution is depicted in conjunction with markings showing a regime (and corresponding filter parameters) that pertains to the inorganic porosity of the reservoir rock from which the third end trim was obtained that contains producible formation water.

Note that FIG. 8 shows the 1D $T_2$ distributions of the first end trim (the native test sample—labeled "Native state"), the second end trim (the resaturated test sample loaded with oil—labeled "Resaturated with oil"), and the third end trim (the resaturated test sample loaded with water-based formation fluid—labeled "Resaturated with water"). FIG. 9 shows the 1D $T_2$ distributions of the second end trim (the resaturated test sample loaded with oil). FIG. 10 shows the 1D $T_2$ distributions of the third end trim (the resaturated test sample loaded with water-based formation fluid).

The $T_2$ values and the $T_1/T_2$ ratios corresponding to those $T_2$ values that particularly relate to the producible oil contained in the organic porosity of the reservoir rock as well as the $T_2$ values and the $T_1/T_2$ ratios corresponding to those $T_2$ values that particularly relate to the inorganic porosity of the reservoir rock can be used to filter NMR data in order to correlate the NMR data to petrophysical properties for the inorganic and organic pore spaces of the resatured unconventional core samples and the reservoir rock from which they are obtained.

For example, the characteristics of the second peak in FIG. 7 and the $T_2$ peak near 2 ms in FIG. 9 correspond to $T_2$ values between 0.5 ms and 10 ms with a $T_1/T_2$ ratio between 3 and 8. These characteristics can be used to define filter parameters ($T_2$ cutoff values and corresponding $T_1/T_2$ ratios) that identify a regime where there are movable/producible oil in the organic pore space of the reservoir rock from which an unconventional core sample is obtained. These filter parameters can be used in conjunction with NMR experiments that produce multidimensional NMR data (e.g., $T_1$, $T_2$, $T_1/T_2$ ratio distributions) for one or more unconventional core samples. The NMR data that falls within the filter parameters can be processed to derive petrophysical properties of the organic pore space of the reservoir rock that contains movable/producible oil. Such petrophysical properties can include porosity, saturation, wettability (such as an Amott-Harvey index or USBM index), pore pressure, and/or other useful properties for the organic pore space of the reservoir rock that contains movable/producible oil. For example, the organic porosity of the reservoir rock that contains movable/producible oil can be derived by summing the $T_2$ distributions that fall within the filter parameters (the $T_2$ cutoff values and corresponding $T_1/T_2$ ratios) corresponding to the regime where there is movable/producible oil in the organic pore space of the reservoir rock. The identity of the fluid and its $T_1/T_2$ ratio together with its $T_2$ value directly implies its wettability state and the environment that it is in. For example, a short $T_2$ of 10 ms and a $T_1/T_2$ ratio of 3-8 for a light oil whose bulk $T_2$ is on the order of 500 ms and $T_1/T_2$ ratio is 1 would mean that it is in an organic pore. The same oil in an inorganic pore will have a $T_1/T_2$ ratio of 1.1-2.2 and a $T_2$ between 10 ms and 100 ms.

Similarly, the characteristics of the third peak in FIG. 7 and the $T_2$ peaks above 10 ms in FIG. 10 correspond to $T_2$ values greater than 10 ms with a $T_1/T_2$ ratio between 1 and 2. These characteristics can be used to define filter parameters ($T_2$ cutoff values and corresponding $T_1/T_2$ ratios) that identify a regime where there is movable/producible oil in the inorganic pore space of the reservoir rock from which an unconventional core sample is obtained. These filter parameters can be used in conjunction with NMR experiments that produces multidimensional NMR data (e.g., $T_1$, $T_2$, $T_1/T_2$ ratio distributions) for one or more unconventional core samples. The NMR data that falls within the filter parameters can be processed to derive petrophysical properties of the inorganic pore space of the reservoir rock that contains movable/producible oil. Such petrophysical properties can include porosity, saturation, wettability (such as an Amott-Harvey index or USBM index), pore pressure, and/or other useful properties for the inorganic pore space of the reservoir rock that contains movable/producible oil. For example, the inorganic porosity that contains movable/producible oil can be derived by summing the $T_2$ distributions that fall within the filter parameters (the $T_2$ cutoff values and corresponding $T_1/T_2$ ratios) corresponding to the regime where there is movable/producible oil in the inorganic pore space of the reservoir rock.

Note that FIGS. 8 and 10 show a $T_2$ peak at 15 ms for the third end trim that is resatured with formation water. This $T_2$ peak relates to producible water that has been re-injected into the pore space of that sample. This $T_2$ peak corresponds to $T_2$ values greater than 4 ms (more preferably between 6 ms and 80 ms) with a $T_1/T_2$ ratio between 1 and 3. These characteristics can be used to define filter parameters ($T_2$ cutoff values and corresponding $T_1/T_2$ ratios) that identify a regime where there is movable/producible water-based formation fluid in the pore space of the reservoir rock from which an unconventional core sample is obtained. These filter parameters can be used in conjunction with NMR experiments that produce multidimensional NMR data (e.g., $T_1$, $T_2$, $T_1/T_2$ ratio distributions) for one or more unconventional core samples. The NMR data that falls within the filter parameters can be processed to derive petrophysical properties of the pore space of the reservoir rock that contains movable/producible water-based formation fluid. Such petrophysical properties can include porosity, saturation, wettability (such as an Amott-Harvey index or USBM index), pore pressure, and/or other useful properties of the pore space of reservoir rock that contains movable/producible water-based formation fluid. For example, the porosity that contains movable/producible water-based formation fluid can be derived by summing the $T_2$ distributions that fall within the filter parameters (the $T_2$ cutoff values and corresponding $T_1/T_2$ ratios) corresponding to the regime where there is movable/producible water-based formation fluid in the pore space of the reservoir rock.

There may be overlap between the pore space that contains producible oil (measured by the analysis of the multidimensional NMR data of the oil resaturated sample) and the pore space that contains producible water (measured by the analysis of multidimensional NMR data of the formation water resaturated sample). This may be particularly true for the inorganic pore space of the reservoir rock, which is typically water-wetting for many tight hydrocarbon reservoirs. This may be addressed by additional solutions such as D-$T_2$ NMR analysis or the application of other logs such as resistivity/dielectric to assist in measuring the contribution of the water-based fluid only, which may then be subtracted from the NMR data as appropriate.

It should be noted that the peaks described herein and the corresponding filter data ($T_2$ values and corresponding $T_1/T_2$ ratios) that particularly relate to the producible oil and water-based formation fluids contained in the pore space of the reservoir rock may shift based on the temperature conditions of the resaturated core sample being tested. For example, performing NMR testing on the resaturated core sample at elevated temperatures at or near reservoir conditions will likely shift the peaks of the corresponding filter data relative to their locations shown in FIGS. 6 and 7. At elevated temperature (approximately 104° C.) the $T_2$ cutoff increases compared to that at ambient temperature and ranges from 1 ms to 23 ms depending on rock type and the $T_1/T_2$ ratio ranges between 1 and 8.

Figure 11A:
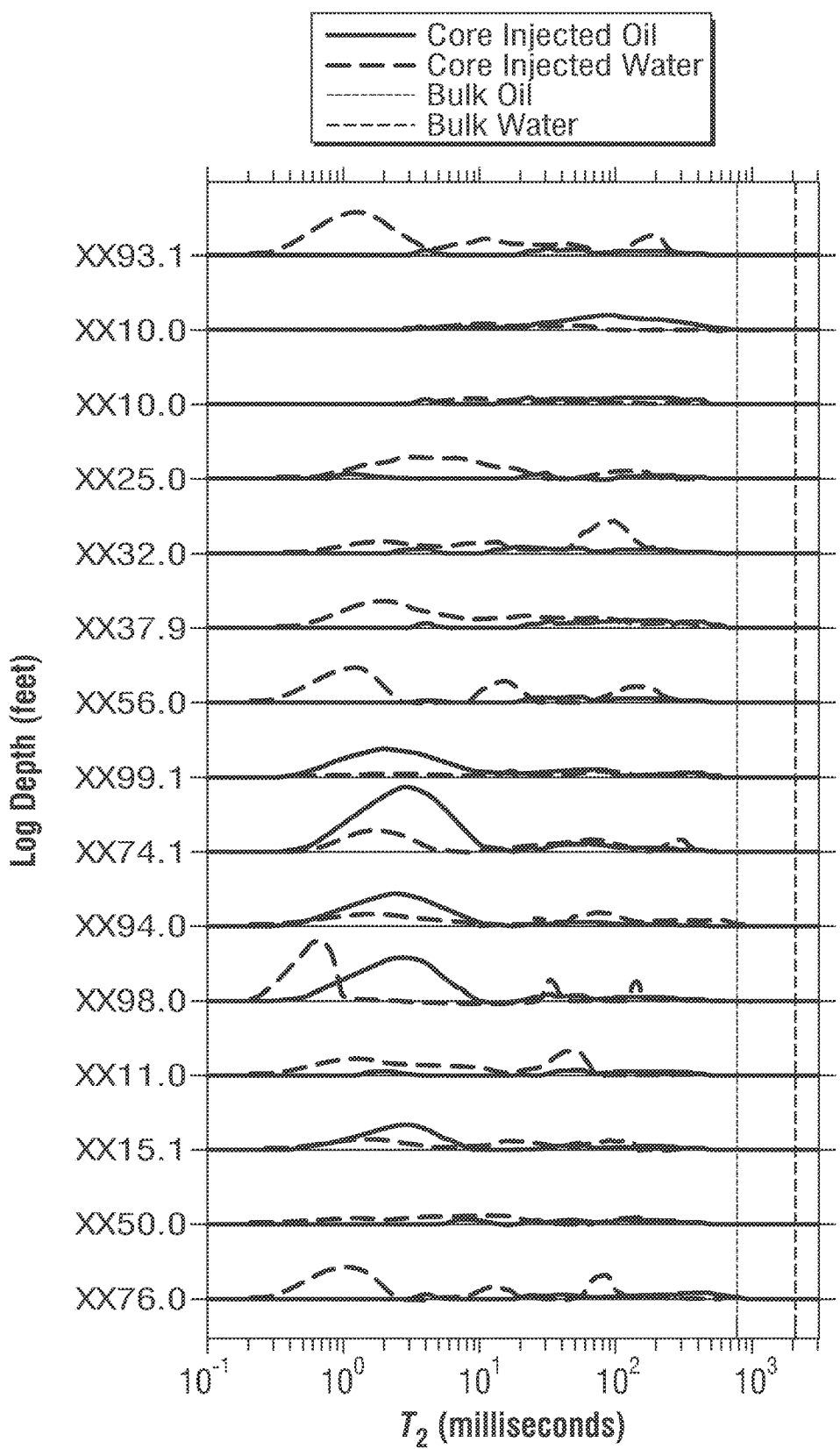
FIGS. 11A and 11B are logs resulting from multidimensional NMR experiments performed on unconventional core samples of reservoir rock obtained from different depths within a tight hydrocarbon reservoir and which have been resaturated with oil and water-based formation fluid, respectively.
Figure 11B:
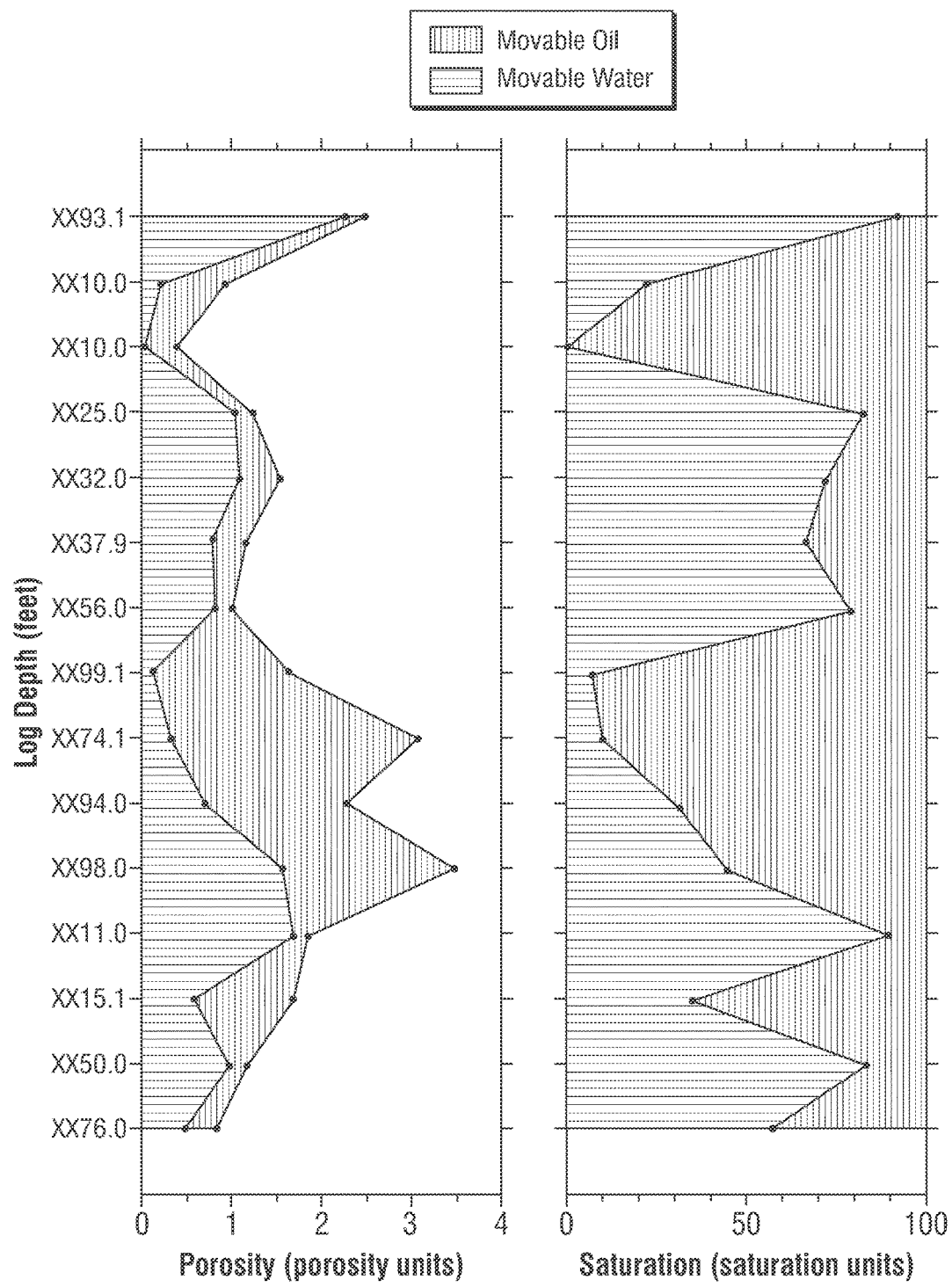

In evaluating a tight hydrocarbon reservoir, the workflow as described herein can be repeated on core samples obtained from different locations in the tight hydrocarbon reservoir under evaluation. In this case, the $T_2$ distributions particularly related to movable oil porosity (or the movable oil porosity itself as derived from such $T_2$ distributions) can be plotted as a function of location in the tight hydrocarbon reservoir under evaluation. The $T_2$ distribution curves (or the movable oil porosity values) that show a relatively high moveable oil porosity at a given location correspond to a sweet spot, which is a target location or area within the tight hydrocarbon reservoir under evaluation that represents the best production or potential production. The $T_2$ distributions particularly related to movable water porosity (or the movable water porosity itself as derived from such $T_2$ distributions) can also be plotted as a function of location in the tight hydrocarbon reservoir under evaluation. This information together with the $T_2$ distributions related to movable oil porosity (or the movable oil porosity itself) reflects the expected water-cut during oil production from the given location. This information can be evaluated at a particular sweet spot to give the expected water-cut during oil production at the sweet spot. An example of such a log is shown in FIG. 11A. The $T_2$ distributions that relate to movable oil porosity as a function of depth in a tight hydrocarbon reservoir under evaluation are labeled "Core Injected Oil". The $T_2$ distributions that relate to movable water porosity as a function of depth in the tight hydrocarbon reservoir under evaluation are labeled "Core Injected Water". The $T_2$ value measured for bulk oil is so labeled. The $T_2$ value measured for bulk water is also so labeled. The $T_2$ distributions that relate to movable oil porosity show a local maximum at depths of xx74.1 to xx98.0 feet, which point to a sweet spot at such locations. Another example of such a log is shown in FIG. 11B. The log on the left shows movable oil porosity and movable water porosity in porosity units as functions of depth in a tight hydrocarbon reservoir under evaluation. The log on the right shows movable oil saturation in saturation units as a function of depth in a tight hydrocarbon reservoir under evaluation. The movable oil porosities show a local maximum at depths of xx74.1 to xx98.0 feet, which point to a "sweet spot" at such locations. The water-cut is the ratio of the movable water porosity to the movable oil porosity. High water-cut areas are generally avoided during completions and areas with high movable oil porosity are chosen for completion.

Furthermore, the multidimensional NMR experiments on the oil and formation water resaturated core samples as described herein can be used as part of a calibration process to derive filter parameters that split the multidimensional NMR data measured from the reservoir rock of the core samples into separate parts that relate to either the oil phase contained in the reservoir rock or the water phase contained in the reservoir rock. In one embodiment, the $T_1$-$T_2$ maps derived from the multidimensional NMR experiments on the oil resaturated and formation water resaturated core samples maps can be plotted as $T_1/T_2$ ratio (y-axis) versus $T_2$ (x-axis) with the $T_2$ distribution quantity (which relates to porosity) coming out of the page. A $(T_1/T_2)_{cutoff}$ line (or "cutoff" for short) that splits the multidimensional NMR data can be optimized by minimizing a predefined function.

In one embodiment, the predefined function involves the calculation of a Residual (cutoff) quantity over a number of depths i for the resaturated core samples as follows:

$$\text{Residual (cutoff)} = \Sigma_i [(\varphi_{Oil}(T_1/T_2 > \text{cutoff}) - \varphi_{Oil})^2 + (\varphi_{Water}(T_1/T_2 < \text{cutoff}) - \varphi_{Water})^2] \quad (1)$$

The quantity $\varphi_{Oil}(T_1/T_2 > \text{cutoff})$ is the partial porosity above the cutoff line for injected oil, which can be derived by integrating the $T_2$ distributions for those $T_1/T_2$ ratios that fall above the cutoff. The quantity $\varphi_{Oil}$ is the total injected oil porosity, which can be derived by the difference between the injected oil porosity and the native state porosity above a given $T_1/T_2$ ratio. Likewise, the quantity $\varphi_{Water}(T_1/T_2 < \text{cutoff})$ is the partial porosity below the cutoff line for injected water, which can be derived by integrating the $T_2$ distributions for those $T_1/T_2$ ratios that fall below the cutoff. The quantity $\varphi_{Water}$ is the total injected water porosity, which can be derived by the difference between the injected water porosity and the native state porosity below a given $T_1/T_2$ ratio. The cutoff is optimized (e.g., adjusted) such that the Residual (cutoff) quantity is minimized over the i depths for the resaturated core samples. The cutoff is assumed to be a straight line on a log-log plot of $T_1/T_2$ ratio versus $T_2$, which translates to the following expression for $T_2$ in units of (ms):

$$(T_1/T_2)_{cutoff} = 8.8 T_2^{-0.23} \quad (2)$$

Note that the cutoff is roughly constant with temperature, i.e., the $T_2$s shift at elevated temperature but the $T_1/T_2$ ratio drops proportionally.

Figure 12:
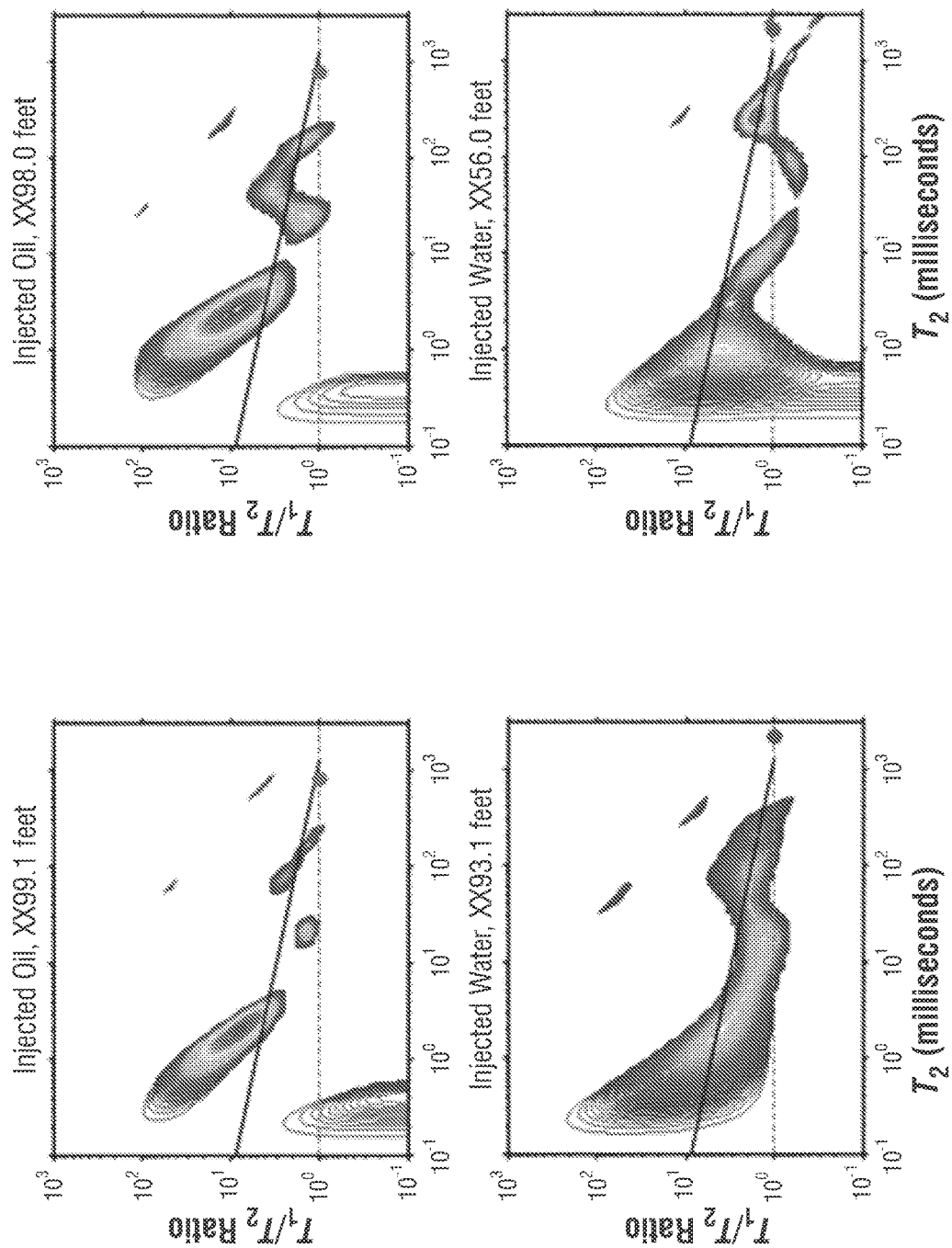
FIG. 12 comprises plots of multidimensional NMR data measured on oil resaturated unconventional core samples of oil-wet reservoir rock (top row), and of multidimensional NMR data measured on water resaturated unconventional core samples of water-wet reservoir rock (bottom row).

FIG. 12 shows some examples of $T_1$-$T_2$ maps for injected oil in oil-wet rocks (top row), and of $T_1$-$T_2$ maps for injected water in water-wet rocks (bottom row). The diagonal line is the optimized $(T_1/T_2)_{cutoff}$ line, while the dashed line is the $T_1/T_2=1$ parity line. The red point is bulk lab oil signal, while the blue point is bulk water signal. The majority of the injected oil signal lies above the $(T_1/T_2)_{cutoff}$ line, while the majority of the injected water signal lies below the $(T_1/T_2)_{cutoff}$ line. This shows that $T_1$-$T_2$ maps provide a clear contrast between oil and water.

Figure 13:
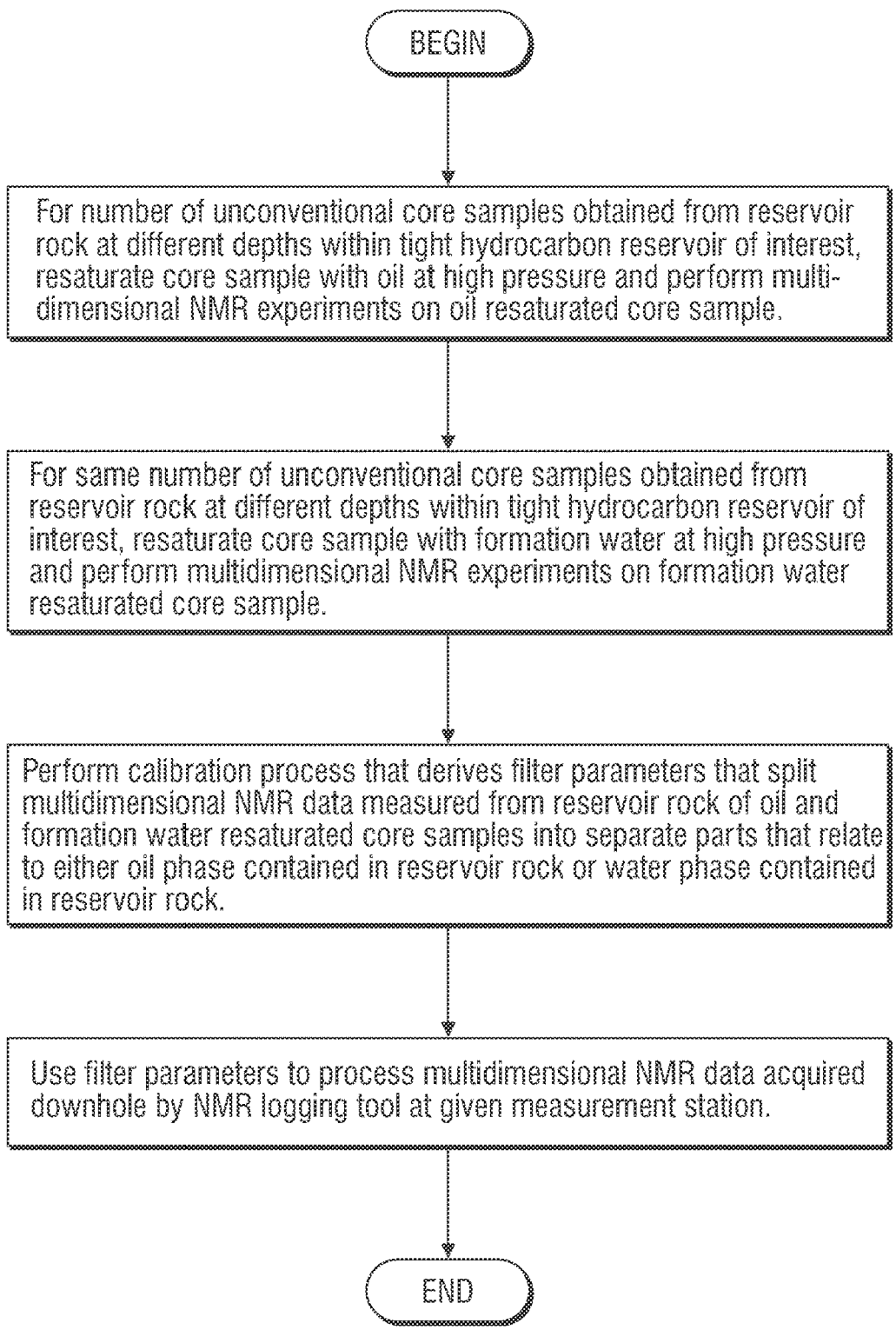
FIG. 13 is a flow chart of an exemplary workflow that performs multidimensional NMR experiments on oil and formation water resaturated unconventional core samples obtained from reservoir rock at different depths within a reservoir of interest as well as a calibration process that derives filter parameters that split the multidimensional NMR data measured from the reservoir rock of the oil and formation water resaturated core samples into separate parts that relate to either the oil phase contained in the reservoir rock or the water phase contained in the reservoir rock; the filter parameters are used to process multidimensional NMR data acquired downhole by an NMR logging tool at a given measurement station.

Given the previous justification for equating injected fluids to movable fluids, the data indicates that the multidimensional NMR experiments and visualization techniques can be used for downhole logging and analysis of movable fluids in a tight hydrocarbon reservoir. In this case, the core resaturation workflow and multidimensional NMR experiments as well as the calibration process on the results of the multidimensional NMR experiments can be used to derive filter parameters for processing the multidimensional NMR data acquired downhole by an NMR logging tool at a given measurement station as shown in the flow chart of FIG. 13.

In one embodiment, the optimized $(T_1/T_2)_{cutoff}$ line can be used to process the multidimensional NMR data acquired downhole by an NMR logging tool for a given measurement station in order to split the multidimensional NMR data into separate parts that relate to either the oil phase contained in the reservoir rock at the measurement station or the water phase contained in the reservoir rock at the measurement station. In this case, the $T_2$ distributions for those $T_1/T_2$ ratios that fall above the optimized $(T_1/T_2)_{cutoff}$ line relate particularly to the oil phase contained in the reservoir rock at the measurement station, and such $T_2$ distributions (or the movable oil porosity itself as derived from such $T_2$ distributions) can be plotted as a function of location in the reservoir under evaluation. Note that $T_2$ distribution curves (or the movable oil porosity values) that show a relatively high movable oil porosity at a given location correspond to a sweet spot, which is a target location or area within the tight hydrocarbon reservoir under evaluation that represents the best production or potential production. Furthermore, the $T_2$ distributions for those $T_1/T_2$ ratios that fall below the optimized $(T_1/T_2)$cutoff line relate particularly to the water phase contained in the reservoir rock at the measurement station, and such $T_2$ distributions (or the movable water porosity itself as derived from such $T_2$ distributions) can also be plotted as a function of location in the tight hydrocarbon reservoir under evaluation. This information together with the $T_2$ distributions related to movable oil porosity (or the movable oil porosity itself) reflects the expected water-cut during oil production from the given location. This information can be evaluated at a particular sweet spot to give the expected water-cut during oil production at the sweet spot. The resulting log would be similar to the red and black curves shown in FIG. 11A.

Some of the methods and processes described above can be implemented as computer program logic for use with a computer processor (e.g., a microprocessor, microcontroller, digital signal processor, or general purpose computer). The computer program logic may be embodied in various forms, including a source code form or a computer-executable form.

Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., Field Programmable Gate Arrays (FPGA)). Any of the methods and processes described above can be implemented using such logic devices.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims.

What is claimed is:

1. A method for testing an unconventional core sample, the method comprising:
   loading the unconventional core sample into a sample holder;
   introducing fluid into the sample holder at an elevated pressure such that fluid is injected into the internal pore space of the unconventional core sample in order to resaturate the unconventional core sample with the fluid, wherein the fluid is selected from the group including a hydrocarbon fluid and a water-based formation fluid; and
   performing analysis on the unconventional core sample resaturated with fluid at the elevated pressure, wherein the analysis derives physical properties of a reservoir rock from which the unconventional core sample was obtained, wherein the physical properties derived from the analysis include at least one property that particularly relates to organic pore space of the reservoir rock that holds producible hydrocarbons;
   wherein the elevated pressure is selected according to at least one of pore size of the unconventional core sample and capillary pressure of the unconventional core sample.

2. The method of claim 1, wherein the elevated pressure is at least 2,000 psig (140.6 kg/square cm gauge).

3. The method of claim 1, further comprising performing analysis on the unconventional core sample resaturated with fluid at elevated pressure, wherein the analysis derives geomechanical and geochemical properties of the reservoir rock from which the unconventional core sample was obtained, wherein the analysis utilizes multidimensional NMR experiments that acquires multidimensional NMR data ($T_1$, $T_2$, D).

4. The method of claim 1, wherein
the fluid is a hydrocarbon fluid.

5. The method of claim 4, wherein the at least one property that particularly relates to organic pore space of the reservoir rock that holds producible hydrocarbons is selected from the group including organic porosity of the reservoir rock that holds producible hydrocarbons, wettability of the organic pore space of the reservoir rock that holds producible hydrocarbons, pore pressure of the organic pore space of the reservoir rock that holds producible hydrocarbons, and hydrocarbon saturation of the organic pore space of the reservoir rock that holds producible hydrocarbons.

6. The method of claim 4, wherein the physical properties derived from the analysis further include at least one property that particularly relates to inorganic pore space of the reservoir rock that holds producible hydrocarbons.

7. The method of claim 6, wherein the at least one property that particularly relates to inorganic pore space of the reservoir rock that holds producible hydrocarbons is selected from the group including inorganic porosity of the reservoir rock that holds producible hydrocarbons, wettability of the inorganic pore space of the reservoir rock that holds producible hydrocarbons, pore pressure of the inorganic pore space of the reservoir rock that holds producible hydrocarbons, and hydrocarbon saturation of the inorganic pore space of the reservoir rock that holds producible hydrocarbons.

8. The method of claim 4, wherein the hydrocarbon fluid is obtained from the reservoir rock from which the unconventional core sample was obtained.

9. The method of claim 1, wherein:
the fluid is a water-based formation fluid; and
the physical properties derived from the analysis include at least one property that particularly relates to inorganic pore space of the reservoir rock that holds producible water-based formation fluid.

10. The method of claim 9, wherein the at least one property that particularly relates to inorganic pore space of the reservoir rock that holds producible water-based formation fluid is selected from the group including inorganic porosity of the reservoir rock that holds producible water-based formation fluid, wettability of the inorganic pore space of the reservoir rock that holds producible water-based formation fluid, pore pressure of the inorganic pore space of the reservoir rock that holds producible water-based formation fluid, and water saturation of the inorganic pore space of the reservoir rock that holds producible water-based formation fluid.

11. The method of claim 9, wherein the water-based formation fluid is brine having a salinity that matches salinity of brine held by the reservoir rock from which the unconventional core sample was obtained.

12. The method of claim 1, wherein the analysis utilizes multidimensional NMR experiments that acquires multidimensional NMR data ($T_1$, $T_2$, D).

13. A method for testing unconventional core samples, the method comprising:
loading a first unconventional core sample into a sample holder;
introducing a hydrocarbon fluid into the sample holder at an elevated pressure such that hydrocarbon fluid is injected into the internal pore space of the first unconventional core sample in order to resaturate the first unconventional core sample with the hydrocarbon fluid;
performing analysis on the first unconventional core sample resaturated with hydrocarbon fluid at the elevated pressure, wherein the analysis derives physical properties of a reservoir rock from which the first unconventional core sample was obtained, wherein the physical properties derived from the analysis include at least one property that particularly relates to organic pore space of the reservoir rock that holds producible hydrocarbons;
loading a second unconventional core sample into a sample holder, wherein the second unconventional core sample is obtained from the same reservoir rock as the first unconventional core sample;
introducing a water-based formation fluid into the sample holder at an elevated pressure such that the water-based formation fluid is injected into the internal pore space of the second unconventional core sample in order to resaturate the second unconventional core sample with the water-based formation fluid; and
performing analysis on the second unconventional core sample resaturated with water-based formation fluid at the elevated pressure, wherein the analysis derives physical properties of the reservoir rock from which the second unconventional core sample was obtained, wherein the physical properties derived from the analysis include at least one property that particularly relates to inorganic pore space of the reservoir rock that holds producible water-based formation fluids;
wherein the analysis performed on both the first and second unconventional core samples utilizes multidimensional NMR experiments that acquires multidimensional NMR data ($T_1$, $T_2$, D).

14. The method of claim 13, wherein the physical properties derived from the analysis performed on the first unconventional core sample further include at least one property that particularly relates to inorganic pore space of the reservoir rock that holds producible hydrocarbons.

15. The method of claim 13, wherein:
the elevated pressure is selected according to at least one of pore size of the first and second unconventional core samples and capillary pressure of the first and second unconventional core samples; and/or
said elevated pressure is at least 2,000 psig (140.6 kg/square cm gauge).

16. A method for testing an unconventional core sample, the method comprising:
loading an unconventional core sample into a sample holder;
introducing a hydrocarbon fluid into the sample holder at an elevated pressure such that the hydrocarbon fluid is injected into the internal pore space of the unconventional core sample in order to resaturate the unconventional core sample with the hydrocarbon fluid;
performing analysis on the unconventional core sample resaturated with hydrocarbon fluid at the elevated pressure, wherein the analysis derives physical properties of a reservoir rock from which the unconventional core sample was obtained, wherein the physical properties derived from the analysis include at least one property that particularly relates to organic pore space of the reservoir rock that holds producible hydrocarbons;
introducing a water-based formation fluid into the sample holder at an elevated pressure such that the water-based formation fluid is injected into the internal pore space of the unconventional core sample in order to resaturate the unconventional core sample with the water-based formation fluid; and performing analysis on the unconventional core sample resaturated with water-based formation fluid at the elevated pressure, wherein the analysis derives physical properties of the reservoir rock from which the unconventional core sample was obtained, wherein the physical properties derived from the analysis include at least one property that particularly relates to inorganic pore space of the reservoir rock that holds producible water-based formation fluids;

wherein the analysis performed on both the first and second unconventional core samples utilizes multidimensional NMR experiments that acquires multidimensional NMR data ($T_1$, $T_2$, D).

17. The method of claim 16, wherein the physical properties derived from the analysis performed on the unconventional core sample resaturated with hydrocarbon fluid further include at least one property that particularly relates to inorganic pore space of the reservoir rock that holds producible hydrocarbons.

18. The method of claim 16, wherein:
the elevated pressure is selected according to at least one of pore size of the unconventional core sample and capillary pressure of the unconventional core sample; and/or
the elevated pressure is at least 2,000 psig (140.6 kg/square cm gauge).

* * * * *